(12) United States Patent
Aurelian et al.

(10) Patent No.: US 7,482,318 B2
(45) Date of Patent: Jan. 27, 2009

(54) PROTEIN KINASE DOMAIN OF THE LARGE SUBUNIT OF HERPES SIMPLEX TYPE 2 RIBONUCLEOTIDE REDUCTASE (ICP 10PK) HAS ANTI-APOPTOTIC ACTIVITY

(75) Inventors: Laure Aurelian, Baltimore, MD (US); Dana Perkins, Gaithersburg, MD (US); Cynthia Smith, Timonium, MD (US)

(73) Assignee: University of Maryland, Baltimore, Baltimore, MD (US)

( * ) Notice: Subject to any disclaimer, the term of this patent is extended or adjusted under 35 U.S.C. 154(b) by 262 days.

(21) Appl. No.: 10/333,607

(22) PCT Filed: Jul. 26, 2001

(86) PCT No.: PCT/US01/23545

§ 371 (c)(1),
(2), (4) Date: Jan. 22, 2003

(87) PCT Pub. No.: WO02/07776

PCT Pub. Date: Jan. 31, 2002

(65) Prior Publication Data

US 2004/0053868 A1      Mar. 18, 2004

Related U.S. Application Data

(60) Provisional application No. 60/221,352, filed on Jul. 26, 2000.

(51) Int. Cl.
*A61K 38/00* (2006.01)
(52) U.S. Cl. .......................................................... 514/2
(58) Field of Classification Search ...................... 514/2
See application file for complete search history.

(56) References Cited

U.S. PATENT DOCUMENTS 5,376,367 A * 12/1994 Williams .................... 424/85.2
5,631,237 A * 5/1997 Dzau et al. ..................... 514/44
5,763,217 A 6/1998 Cynader et al.
5,834,309 A * 11/1998 Thompson et al. .......... 435/325
5,922,328 A 7/1999 Spector et al.

FOREIGN PATENT DOCUMENTS

WO    WO 98/22608       5/1998
WO    WO 00/07618       2/2000
WO    WO0023083 A1 *    4/2000

OTHER PUBLICATIONS

Shire in Biopharmaceutical Drug Design and Development (Wu-pong et al. Eds, Humana Press; Chapter 9; pp. 205-238; 1999).*
Perkins et al., "ICP10PK anti-apoptotic activity and CNS resistance to herpes simplex type 2 (HSV-2) infection"; Society for Neuroscience Abstracts, vol. 26, No. 1-2, Nov. 2000 (New Orleans, LA, USA), see abstract No. 398.9, p. 1062.
Keith R. Jerome et al., "Herpes Simplex Virus Inhibits Apoptosis through the Action of Two Genes, Us5 and Us3", Journal of Virology, Nov. 1999, pp. 8950-8957; vol. 73; No. 11.
D. Perkins et al.; "The Herpes Simplex Virus Type 2 R1 Protein Kinase (ICP10 PK) Blocks Apoptosis in Hippocampal Heurons, Involving Activation of the MEK/MAPK Survival Pathway"; Journal of Virology, Feb. 2002, pp. 1435-1449; vol. 76, No. 3.
James Colin Ramsay Hunter, Neoplastic Transformation, Cellular Localization and Protein Kinase Activity of the RR1 Subunit of Herpes Simplex Virus Type 2 (ICP10); May 13, 1996; Dissertation submitted to the Faculty of the Graduate School of the University of Maryland.

* cited by examiner

*Primary Examiner*—J. E Angell
(74) *Attorney, Agent, or Firm*—Millen, White, Zelano & Branigan, P.C.

(57) ABSTRACT

The invention relates to a method of treating neuronal apoptosis in a mammal using nucleic acid encoding HSV-2 ICP10PK, or a polypeptide encoded thereby. The invention further relates to a method of treating neuronal apoptosis in a mammal using ICP10PK in combination with a nucleic acid encoding bcl-2, or the polypeptide encoded thereby. The invention also relates to the use of ICP10PK and ICP10PK in combination with bcl-2 to treat non-neuronal diseases characterized by apoptosis.

9 Claims, 21 Drawing Sheets

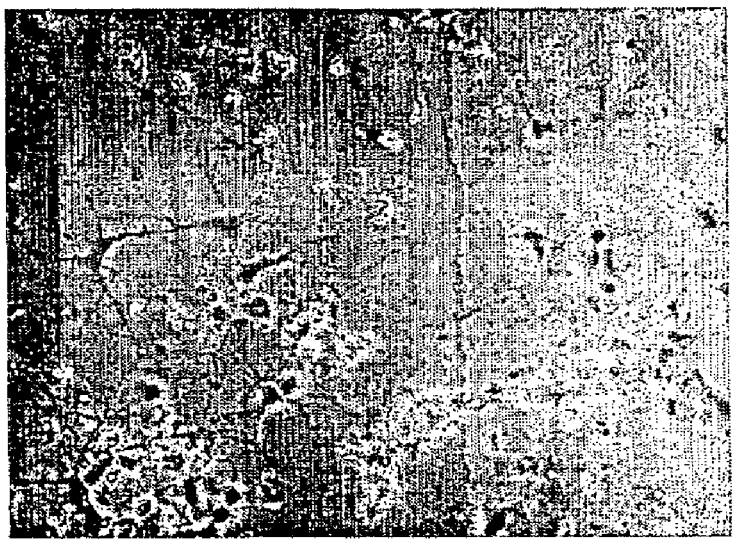
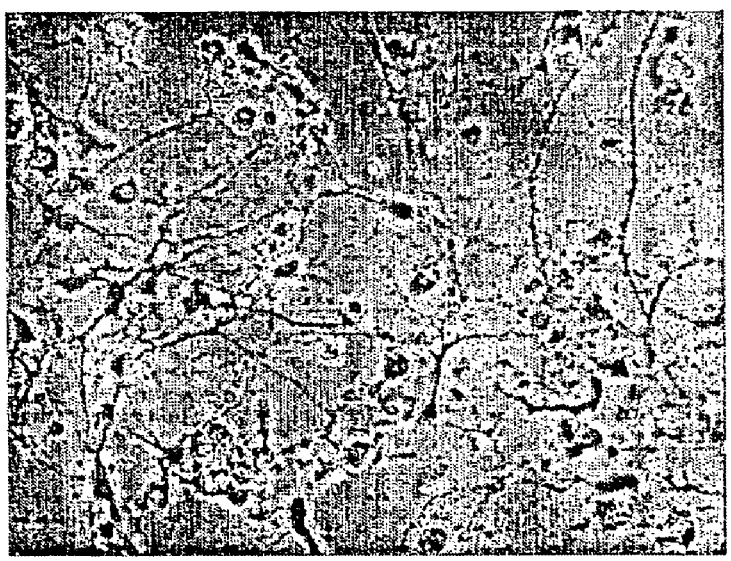
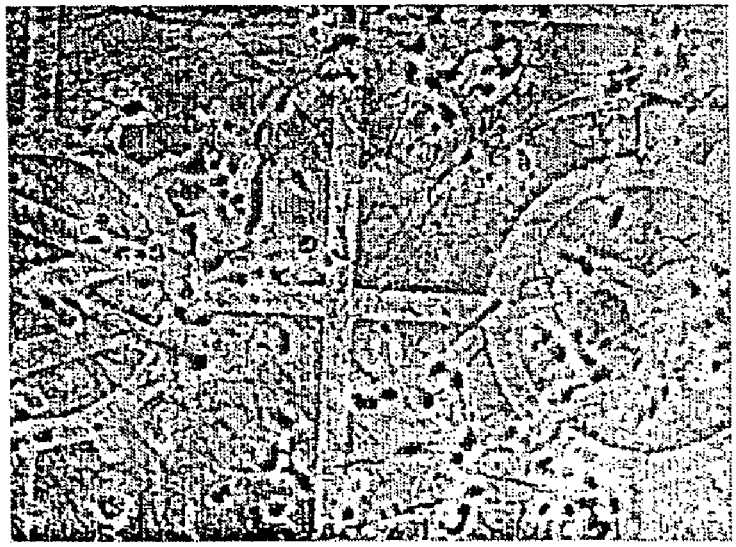
FIG.14C
FIG.14B
FIG.14A

SEQUENCE LISTING

<160> NUMBER OF SEQ ID NOS: 2

<210> SEQ ID NO 1
<211> LENGTH: 5956
<212> TYPE: DNA
<213> ORGANISM: herpes simplex virus type 2

<400> SEQUENCE: 1

```
gtgtgtttgg cgtgtgtctc tgaaatggcg gaaaccgaca tgcaaatggg attcatggac        60
acgttacacc cccctgactc aggagatagg catatcctcc ttagattgac tcagcacacg       120
atcgcacccc acccctgtgt gccggggata aaagccaacg cgggcggtct gggttaccac       180
aacaggtggg tgcttcgggg acttgacggt cgccactctc ctgcgagccc tcacgtcttc       240
gcccaccgat tcctgttgcg ttcctgtcgg ccggtgctgt cctgtcgaca gattgttggc       300
gactgcccgg gtgattcgtc ggccggtgcg tcctttcggt cgtaccgccc accccgcctc       360
ccacgggccc gccgctgttt ccgttcatcg cgtccgagcc accgtcacct tggttccaat       420
ggccaaccgc cctgccgcat ccgccctcgc cggagcgcgg tctccgtccg aacgacagga       480
accccgggag cccgaggtcg ccccccctgg cggcgaccac gtgttttgca ggaaagtcag       540
cggcgtgatg gtgctttcca gcgatccccc cggccccgcg gcctaccgca ttagcgacag       600
cagctttgtt caatgcggct ccaactgcag tatgataatc gacggagacg tggcgcgcgg       660
tcatttgcgt gacctcgagg gcgctacgtc caccggcgcc ttcgtcgcga tctcaaacgt       720
cgcagccggc ggggatggcc gaaccgccgt cgtggcgctc ggcggaacct cgggcccgtc       780
cgcgactaca tccgtgggga cccagacgtc cggggagttc ctccacggga acccaaggac       840
ccccgaaccc caaggacccc aggctgtccc ccgcccccct cctccccccct ttccatgggg       900
ccacgagtgc tgcgcccgtc gcgatgccag gggcggcgcc gagaaggacg tcggggccgc       960
ggagtcatgg tcagacggcc cgtcgtccga ctccgaaacg gaggactcgg actcctcgga      1020
cgaggatacg ggctcgggtt cggagacgct gtctcgatcc tcttcgatct gggccgcagg      1080
ggcgactgac gacgatgaca gcgactccga ctcgcggtcg gacgactccg tgcagcccga      1140
cgttgtcgtt cgtcgcagat ggagcgacgg ccctgccccc gtggccttc ccaagccccg       1200
gcgcccggc gactccccg gaaacccgg cctgggcgcc ggcaccgggc cgggctccgc         1260
gacggacccg cgcgcgtcgg ccgactccga ttccgcggcc cacgccgccg caccccaggc      1320
ggacgtggcg ccggttctgg acagccagcc cactgtggga acggacccg gctacccagt       1380
ccccctagaa ctcacgcccg agaacgcgga ggcggtggcg cggtttctgg gggacgccgt      1440
cgaccgcgag cccgcgctca tgctggagta cttctgtcgg tgcgcccgcg aggagagcaa      1500
gcgcgtgccc ccacgaacct tcggcagcgc ccccgcctc acggaggacg actttgggct       1560
cctgaactac gcgctcgctg agatgcgacg cctgtgcctg gacttccccc ggtcccccc       1620
caacgcatac acgccctatc atctgaggga gtatgcgacg cggctggtta acggggttcaa     1680
accccctggtg cggcggtccg cccgcctgta tcgcatcctg gggattctgg ttcacctgcg     1740
catccgtacc cgggaggcct cctttgagga atggatgcgc tccaaggagg tggacctgga      1800
cttcgggctg acgaaaaggc ttcgcgaaca cgaggcccag ctaatgatcc tggcccaggc      1860
cctgaacccc tacgactgtc tgatccacag caccccgaac acgtcgtcg agcggggct        1920
gcagtcggcg ctgaagtacg aagagttttta cctcaagcgc ttcggcgggc actacatgga    1980
gtccgtcttc cagatgtaca cccgcatcgc cgggttcctg gcgtgccggg cgacccgcgg     2040
catgcgccac atcgccctgg ggcgacaggg gtcgtggtgg gaaatgttca gttctttttt      2100
ccaccgcctc tacgaccacc agatcgtgcc gtccaccccc gccatgctga acctcggaac      2160
ccgcaactac tacacgtcca gctgctacct ggtaaacccc caggccacca ctaaccaggc      2220
cacccctccgg gccatcaccg gcaacgtgag cgccatcctc gcccgcaacg ggggcatcgg    2280
```

```
gctgtgcatg caggcgttca acgacgccag ccccggcacc gccagcatca tgccggccct   2340
gaaggtcctg gactccctgg tggcggcgca caacaaacag agcacgcgcc ccaccggggc   2400
gtgcgtgtac ctggaaccct ggcacagcga cgttcgggcc gtgctcagaa tgaagggcgt   2460
cctcgccggc gaggaggccc agcgctgcga caacatcttc agcgccctct ggatgccgga   2520
cctgttcttc aagcgcctga tccgccacct cgacggcgag aaaaacgtca cctggtccct   2580
gttcgaccgg gacaccagca tgtcgctcgc cgactttcac ggcgaggagt tcgagaagct   2640
gtacgagcac ctcgaggcca tggggttcgg cgaaacgatc cccatccagg acctggcgta   2700
cgccatcgtg cgcagcgcgg ccaccaccgg aagccccttc atcatgttta aggacgcggt   2760
aaaccgccac tacatctacg acacgcaagg ggcggccatt gccggctcca acctctgcac   2820
ggagatcgtc caccccgtcct ccaaacgctc agcggggtc tgcaacctgg cagcgtgaa   2880
tctggcccga tgcgtctccc ggcggacgtt cgattttggc atgctccgcg acgccgtgca   2940
ggcgtgcgtg ctaatggtta atatcatgat agacagcacg ctgcagccga cgccccagtg   3000
cgcccgcggc cacgacaacc tgcggtccat gggcattggc atgcagggcc tgcacacggc   3060
gtgcctgaag atgggcctgg atctggagtc ggccgagttc cgggacctga acacacacat   3120
cgccgaggtg atgctgctcg cggccatgaa gaccagtaac gcgctgtgcg ttcgcggggc   3180
gcgtcccttc agccacttta agcgcagcat gtaccgggcc ggccgctttc actgggagcg   3240
cttttcgaac gccagcccgc ggtacgaggg cgagtgggag atgctacgcc agagcatgat   3300
gaaacacggc ctgcgcaaca gccagttcat cgcgctcatg cccaccgccg cctcggccca   3360
gatctcggac gtcagcgagg gctttgcccc cctgttcacc aacctgttca gcaaggtgac   3420
cagggacggc gagacgctgc gccccaacac gctcttgctg aaggaactcg agcgcacgtt   3480
cggcgggaag cggctcctgg acgcgatgga cgggctcgag gccaagcagt ggtctgtggc   3540
ccaggccctg ccttgcctgg accccgccca ccccctccgg cggttcaaga cggccttcga   3600
ctacgaccag gaactgctga tcgacctgtg tgcagaccgc gcccctatg ttgatcacag   3660
ccaatccatg actctgtatg tcacagagaa ggcggacggg acgctccccg cctccacccct  3720
ggtccgcctt ctcgtccacg catataagcg cggcctgaag acggggatgt actactgcaa   3780
ggttcgcaag gcgaccaaca gcggggtgtt cgccggcgac gacaacatcg tctgcacaag   3840
ctgcgcgctg taagcaacag cgctccgatc ggggtcaggc gtcgctctcg gtcccgcata   3900
tcgccatgga tcccgccgtc tccccgcgca gcaccgaccc cctagatacc cacgcgtcgg   3960
gggcgggggc ggccccgatt ccggtgtgcc ccaccccga gcggtacttc tacacctccc   4020
agtgccccga catcaaccac cttcgctccc tcagcatcct gaaccgctgg ctggagaccg   4080
agctcgtgtt cgtgggggac gaggaggacg tctccaagct ctccgagggc gagctcggct   4140
tctaccgctt tctgtttgcc ttcctgtcgg ccgcggacga cctggtgacg gaaaacctgg   4200
gcggcctctc cggcctcttc gaacagaagg acattcttca ctactacgtg gagcaggaat   4260
gcatcgaggt cgtccactcg cgcgtctaca acatcatcca gctggtgctc tttcacaaca   4320
acgaccaggc gcgccgcgcc tatgtggccc gcaccatcaa ccaccggcc attcgcgtca   4380
aggtggactg gctggaggcg cgggtgcggg aatgcgactc gatcccggag aagttcatcc   4440
tcatgatcct catcgagggc gtcttttttg ccgcctcgtt cgccgccatc gcgtacctgc   4500
gcaccaacaa cctcctgcgg gtcacctgcc agtcgaacga cctcatcagc cgcgacgagg   4560
ccgtgcatac gacagcctcg tgctacatct acaacaacta cctcggggc cacgccaagc   4620
ccgaggcggc gcgcgtgtac cggctgtttc gggaggcggt ggatatcgag atcgggttca   4680
```

-continued

```
tccgatccca ggccccgacg gacagctcta tcctgagtcc gggggccctg gcggccatcg    4740
agaactacgt gcgattcagc gcggatcgcc tgctgggcct gatccatatg cagcccctgt    4800
attccgcccc cgccccgac gccagctttc cctcagcct catgtccacc gacaaacaca      4860
ccaacttctt cgagtgccgc agcacctcgt acgccgggc cgtcgtcaac gatctgtgag     4920
ggtctgggcg cccttgtagc gatgtctaac cgaaataaag gggtcgaaac ggactgttgg    4980
gtctccggtg tgattattac gcaggggagg ggggtggcgg ctggggaaag gaaggaacg     5040 cccgaaacca gagaaaagga ccaaaaggga acgcgtcca accgataaat caagcgccga    5100
ccagaacccc gagatgcata ataacaaacg attttattac tcttattatt aacaggtcgg    5160
gcatcgggag gggatggggg cgcgcgtttc ctccgttccg gctactcgtc ccagaattta    5220
gccaggacgt ccttgtaaaa cgcgggcggg ggcgcgtggg cccacagctg cgccagaaac    5280
cggtcggcga tgtccggggc ggtgatatgc cgagtcacga tggagcgcgc taaatcttcg    5340
tcgcggaggt cctgatagat gggcagtctt tttagaagag tccagggtcc ccgctccttg    5400
gggctgataa gcgatatgac gtacttgacg tatctgtgct ccaccagctc ggcgatggtc    5460
atcggatcgg gcagccagtc cagggcctcc ggggcgtcgt ggatgacgtg gcggcgacgt    5520
ccggcgacat agccgcggtg ttccgcgacc cgctgcgcgt tggggacctg cacgagctcg    5580
ggcggggtga gtatctccga ggaggacgac cgggcgccgt cgcgcggccc accggcgacg    5640
tccgggggct ggaggggggg gtcttcttcg tagtcgtcct cgcccgcgat ctgttgggcc    5700
agaatttcgg tccacgagat gcgcgtctcg aggccgaccg gggccgcggt cagcgtaggc    5760
atgctctcca gggagcgcga gttggcgcgc tcccgccggg ccgcccggcg ggcctgggat    5820
cggctcgggg cggtccagtg acactcgcgc agcacgtcct cgacggacgc gtaggtgtta    5880
ttggggtgca ggtctgtgtg gcagcggacg aacagcgcca ggaactgcgg gtaactcatc    5940
ttgaagtacc ctgcag                                                    5956
```

<210> SEQ ID NO 2
<211> LENGTH: 1144
<212> TYPE: PRT
<213> ORGANISM: herpes simplex virus type 2

<400> SEQUENCE: 2

```
Met Ala Asn Arg Pro Ala Ala Ser Ala Leu Ala Gly Ala Arg Ser Pro
  1               5                  10                  15

Ser Glu Arg Gln Glu Pro Arg Glu Pro Glu Val Ala Pro Gly Gly
             20                  25                  30

Asp His Val Phe Cys Arg Lys Val Ser Gly Val Met Val Leu Ser Ser
         35                  40                  45

Asp Pro Pro Gly Pro Ala Ala Tyr Arg Ile Ser Asp Ser Ser Phe Val
     50                  55                  60

Gln Cys Gly Ser Asn Cys Ser Met Ile Ile Asp Gly Asp Val Ala Arg
 65                  70                  75                  80

Gly His Leu Arg Asp Leu Glu Gly Ala Thr Ser Thr Gly Ala Phe Val
                 85                  90                  95

Ala Ile Ser Asn Val Ala Ala Gly Gly Asp Gly Arg Thr Ala Val Val
            100                 105                 110

Ala Leu Gly Gly Thr Ser Gly Pro Ser Ala Thr Thr Ser Val Gly Thr
        115                 120                 125

Gln Thr Ser Gly Glu Phe Leu His Gly Asn Pro Arg Thr Pro Glu Pro
    130                 135                 140
```

-continued

```
Gln Gly Pro Gln Ala Val Pro Pro Pro Pro Pro Pro Phe Pro Trp
145                 150                 155                 160

Gly His Glu Cys Cys Ala Arg Arg Asp Ala Arg Gly Gly Ala Glu Lys
            165                 170                 175

Asp Val Gly Ala Ala Glu Ser Trp Ser Asp Gly Pro Ser Ser Asp Ser
        180                 185                 190

Glu Thr Glu Asp Ser Asp Ser Ser Asp Glu Asp Thr Gly Ser Gly Ser
    195                 200                 205

Glu Thr Leu Ser Arg Ser Ser Ser Ile Trp Ala Ala Gly Ala Thr Asp
    210                 215                 220

Asp Asp Asp Ser Asp Ser Asp Ser Arg Ser Asp Asp Ser Val Gln Pro
225                 230                 235                 240

Asp Val Val Val Arg Arg Arg Trp Ser Asp Gly Pro Ala Pro Val Ala
                245                 250                 255

Phe Pro Lys Pro Arg Arg Pro Gly Asp Ser Pro Gly Asn Pro Gly Leu
            260                 265                 270

Gly Ala Gly Thr Gly Pro Gly Ser Ala Thr Asp Pro Arg Ala Ser Ala
        275                 280                 285

Asp Ser Asp Ser Ala Ala His Ala Ala Ala Pro Gln Ala Asp Val Ala
    290                 295                 300

Pro Val Leu Asp Ser Gln Pro Thr Val Gly Thr Asp Pro Gly Tyr Pro
305                 310                 315                 320

Val Pro Leu Glu Leu Thr Pro Glu Asn Ala Glu Ala Val Ala Arg Phe
                325                 330                 335

Leu Gly Asp Ala Val Asp Arg Glu Pro Ala Leu Met Leu Glu Tyr Phe
            340                 345                 350

Cys Arg Cys Ala Arg Glu Glu Ser Lys Arg Val Pro Pro Arg Thr Phe
        355                 360                 365

Gly Ser Ala Pro Arg Leu Thr Glu Asp Asp Phe Gly Leu Leu Asn Tyr
    370                 375                 380

Ala Leu Ala Glu Met Arg Arg Leu Cys Leu Asp Leu Pro Pro Val Pro
385                 390                 395                 400

Pro Asn Ala Tyr Thr Pro Tyr His Leu Arg Glu Tyr Ala Thr Arg Leu
                405                 410                 415

Val Asn Gly Phe Lys Pro Leu Val Arg Arg Ser Ala Arg Leu Tyr Arg
            420                 425                 430

Ile Leu Gly Ile Leu Val His Leu Arg Ile Arg Thr Arg Glu Ala Ser
        435                 440                 445

Phe Glu Glu Trp Met Arg Ser Lys Glu Val Asp Leu Asp Phe Gly Leu
    450                 455                 460

Thr Glu Arg Leu Arg Glu His Glu Ala Gln Leu Met Ile Leu Ala Gln
465                 470                 475                 480

Ala Leu Asn Pro Tyr Asp Cys Leu Ile His Ser Thr Pro Asn Thr Leu
                485                 490                 495

Val Glu Arg Gly Leu Gln Ser Ala Leu Lys Tyr Glu Glu Phe Tyr Leu
            500                 505                 510

Lys Arg Phe Gly Gly His Tyr Met Glu Ser Val Phe Gln Met Tyr Thr
        515                 520                 525

Arg Ile Ala Gly Phe Leu Ala Cys Arg Ala Thr Arg Gly Met Arg His
    530                 535                 540

Ile Ala Leu Gly Arg Gln Gly Ser Trp Trp Glu Met Phe Lys Phe Phe
545                 550                 555                 560
```

-continued

```
Phe His Arg Leu Tyr Asp His Gln Ile Val Pro Ser Thr Pro Ala Met
            565                 570                 575

Leu Asn Leu Gly Thr Arg Asn Tyr Tyr Thr Ser Ser Cys Tyr Leu Val
            580                 585                 590

Asn Pro Gln Ala Thr Thr Asn Gln Ala Thr Leu Arg Ala Ile Thr Gly
            595                 600                 605

Asn Val Ser Ala Ile Leu Ala Arg Asn Gly Gly Ile Gly Leu Cys Met
610                 615                 620

Gln Ala Phe Asn Asp Ala Ser Pro Gly Thr Ala Ser Ile Met Pro Ala
625                 630                 635                 640

Leu Lys Val Leu Asp Ser Leu Val Ala Ala His Asn Lys Gln Ser Thr
                645                 650                 655

Arg Pro Thr Gly Ala Cys Val Tyr Leu Glu Pro Trp His Ser Asp Val
            660                 665                 670

Arg Ala Val Leu Arg Met Lys Gly Val Leu Ala Gly Glu Glu Ala Gln
            675                 680                 685

Arg Cys Asp Asn Ile Phe Ser Ala Leu Trp Met Pro Asp Leu Phe Phe
690                 695                 700

Lys Arg Leu Ile Arg His Leu Asp Gly Lys Asn Val Thr Trp Ser
705                 710                 715                 720

Leu Phe Asp Arg Asp Thr Ser Met Ser Leu Ala Asp Phe His Gly Glu
                725                 730                 735

Glu Phe Glu Lys Leu Tyr Glu His Leu Glu Ala Met Gly Phe Gly Glu
            740                 745                 750

Thr Ile Pro Ile Gln Asp Leu Ala Tyr Ala Ile Val Arg Ser Ala Ala
            755                 760                 765

Thr Thr Gly Ser Pro Phe Ile Met Phe Lys Asp Ala Val Asn Arg His
            770                 775                 780

Tyr Ile Tyr Asp Thr Gln Gly Ala Ala Ile Ala Gly Ser Asn Leu Cys
785                 790                 795                 800

Thr Glu Ile Val His Pro Ser Ser Lys Arg Ser Ser Gly Val Cys Asn
                805                 810                 815

Leu Gly Ser Val Asn Leu Ala Arg Cys Val Ser Arg Thr Phe Asp
            820                 825                 830

Phe Gly Met Leu Arg Asp Ala Val Gln Ala Cys Val Leu Met Val Asn
            835                 840                 845

Ile Met Ile Asp Ser Thr Leu Gln Pro Thr Pro Gln Cys Ala Arg Gly
850                 855                 860

His Asp Asn Leu Arg Ser Met Gly Ile Gly Met Gln Gly Leu His Thr
865                 870                 875                 880

Ala Cys Leu Lys Met Gly Leu Asp Leu Glu Ser Ala Glu Phe Arg Asp
                885                 890                 895

Leu Asn Thr His Ile Ala Glu Val Met Leu Leu Ala Ala Met Lys Thr
            900                 905                 910

Ser Asn Ala Leu Cys Val Arg Gly Ala Arg Pro Phe Ser His Phe Lys
            915                 920                 925

Arg Ser Met Tyr Arg Ala Gly Arg Phe His Trp Glu Arg Phe Ser Asn
930                 935                 940

Ala Ser Pro Arg Tyr Glu Gly Glu Trp Glu Met Leu Arg Gln Ser Met
945                 950                 955                 960

Met Lys His Gly Leu Arg Asn Ser Gln Phe Ile Ala Leu Met Pro Thr
                965                 970                 975

Ala Ala Ser Ala Gln Ile Ser Asp Val Ser Glu Gly Phe Ala Pro Leu
```

```
                     -continued
            980              985              990
Phe Thr Asn Leu Phe Ser Lys Val Thr Arg Asp Gly Glu Thr Leu Arg
        995                 1000            1005

Pro Asn Thr Leu Leu Leu Lys Glu Leu Glu Arg Thr Phe Gly Gly Lys
    1010                1015            1020

Arg Leu Leu Asp Ala Met Asp Gly Leu Glu Ala Lys Gln Trp Ser Val
1025            1030            1035            1040

Ala Gln Ala Leu Pro Cys Leu Asp Pro Ala His Pro Leu Arg Arg Phe
            1045            1050            1055

Lys Thr Ala Phe Asp Tyr Asp Gln Glu Leu Leu Ile Asp Leu Cys Ala
            1060            1065            1070

Asp Arg Ala Pro Tyr Val Asp His Ser Gln Ser Met Thr Leu Tyr Val
        1075            1080            1085

Thr Glu Lys Ala Asp Gly Thr Leu Pro Ala Ser Thr Leu Val Arg Leu
    1090            1095            1100

Leu Val His Ala Tyr Lys Arg Gly Leu Lys Thr Gly Met Tyr Tyr Cys
1105            1110            1115            1120

Lys Val Arg Lys Ala Thr Asn Ser Gly Val Phe Ala Gly Asp Asp Asn
            1125            1130            1135

Ile Val Cys Thr Ser Cys Ala Leu
            1140
```

PROTEIN KINASE DOMAIN OF THE LARGE SUBUNIT OF HERPES SIMPLEX TYPE 2 RIBONUCLEOTIDE REDUCTASE (ICP 10PK) HAS ANTI-APOPTOTIC ACTIVITY

This application claims the benefit of the filing date of U.S. Provisional Application Ser. No. 60/221,352 filed Jul. 26, 2000.

BACKGROUND OF THE INVENTION

The lack of effective treatment for a number of neurological diseases, many of which are fatal, is a significant public health concern. Approximately four million Americans have Alzheimer's disease (AD) and the number will increase to approximately fourteen million by the year 2005, unless a cure or prevention is found. Similarly, amyotrophic lateral sclerosis (ALS), commonly known as Lou Gherig's disease, is a fatal neurodegenerative disease that affects approximately 2 per 100,000 people. In the U.S. alone, more than 5,000 people are diagnosed with ALS each year. Approximately 15 million people in the U.S. suffer from diabetes, and most are at risk for development of neuropathy associated with diabetes. The incidence of diabetic neuropathy is considered to be 6 in 10,000 people. Down syndrome (DS), which occurs in 1 of 1,000 live births, also causes severe developmental brain abnormalities. Moreover, DS patients develop AD by their fifth decade of life. The common denominator for neurodegenerative disorders (which also include Parkinson's disease (PD) and Huntington disease (HD)) is selective neuronal loss due to programmed cell death or apoptosis. To date, there are no known cures or effective treatments for these diseases. Acute neurological diseases involving apoptotic death offer a window of opportunity for short-term treatment. They include stroke, trauma and hypoxia-ischemia, where there is a delayed "secondary" brain injury in a "penumbra zone", that is initially spared and surrounds the area of most severe damage. Cell death in these penumbra areas is due to apoptosis and is amenable to anti-apoptotic therapeutic strategies that minimize brain damage. While stroke is the third common cause of death in the US, it is a leading cause of long-term disability. Over 400,000 subjects suffer from a first ischemic stroke each year in the US. Effective treatment is not currently available, and gene therapy is limited by the paucity of genes with anti-apoptotic activity in the CNS.

Following spinal cord injury (SCI), loss of motor neurons occurs by mechanical tissue disruption as well as necrosis. Secondarily, degeneration results from a cascade of events triggered by the injury and results in the activation of endogenous apoptosis, cell death. Apoptosis does not occur immediately after injury; rather it occurs over a prolonged period of several weeks. The cause of the apoptosis includes loss of trophic support, intracellular oxidative stress including oxidative damage to, and activation of caspases including caspase-q and caspase-3 in both neurons and microglia. Moreover an increase in the expression of pro-apoptotic peptide Bax and a reciprocal decrease in the anti-apoptotic Bcl-2 peptide in the mitochondrial-enriched membrane compartments occurs with SCI. Such a loss of motor neurons causes paralysis and death.

Apoptosis is a normal physiological process observed in many cell types and enables useful pruning of "mismatched" or excessive cells during development and maturation. Apoptosis is critical to modeling of the nervous system during embryonic development and in the regulation and function of the immune system. However, cellular homeostasis is dependent on a proper balance between survival/proliferation and apoptotic processes. Thus, excessive apoptosis can lead to non-physiological death, and ultimately to disease states. In the adult nervous system, where there is little cell production and little cell death, excessive apoptosis results in neurological diseases including AD, ALS, DS, PD, and HD, or is subsequent to physical ischemic or chemical injury of the central nervous system (CNS). What exactly prompts apoptosis in chronic disorders is unclear, but several stimuli are thought to play an etiologic role. Such stimuli include oxidative stress that may increase with age, loss of neurotrophic support, accumulated burden of endogenous and exogenous factors, and excessive release of neurotransmitters known as excitotoxins.

Features associated with apoptosis include cell shrinkage, exposure of phosphatidylserine on the outer surface of the membrane, plasma membrane blebbing, mitochondrial dysfunction, DNA cleavage, chromatin condensation, and formation of membrane bound apoptotic bodies. Apoptosis involves three phases: (i) a time-variable phase called commitment which refers to the time from the reception of apoptotic stimuli to the irreversible initiation of the second phase, (ii) execution phase in which all of the dramatic changes associated with cell death occur, and (iii) clearance, which involves engulfment of apoptotic bodies by neighboring cells or be professional phagocytes without the stimulation of an inflammatory response. The commitment phase is influenced by the proliferative status of the cell, cell type, apoptotic stimulus and expression of regulatory genes that inhibit or promote apoptosis. During the commitment phase, a cell is faced with multiple decision/check points. The nature and intensity of the incoming stimulus may determine whether the cell survives (if the defense mechanisms can overcome the insult) or commits to undergo a series of apoptotic phases. This death is characterized by several morphological changes including condensation of the cell nucleus and membrane blebbing. In addition, there is DNA fragmentation caused by a group of caspases (cysteine aspartases) that are specifically activated in apoptotic cells by proteolytic cleavage. Indeed, the execution process of apoptosis occurs mainly via activation of a series of proteolytic enzymes, termed caspases. Once active, caspases cleave a number of cellular proteins including proteins involved in DNA repair and replication such as poly (ADP-ribose) polymerase (PARP), DNA-dependent protein kinase (DNA-PK), and Inhibitors of Caspase-Activated DNAse (ICAD), as well as structural proteins, thereby inducing endonuclease activation and the characteristic morphological changes associated with apoptosis.

Caspase-3 is one of the key executioners of apoptosis. Its activation requires proteolytic cleavage of the inactive pro-caspase-3 into activated 17-20 kDa and 12 kDa subunits. Activated caspase-3 is, in turn, responsible, either partially or totally, for the proteolytic cleavage of many key proteins, such as PARP, that is involved in DNA repair. PARP cleavage is a crucial event in the commitment to undergo apoptosis. Again, cell homeostasis depends on the balance between apoptotic and survival/proliferation processes. Survival stimuli cause the membrane bound G protein, Ras, to adopt an active, GTP-bound state, and it, in turn, coordinates the activation of a multitude of downstream effectors. The mitogenic/survival Ras/MEK/MAPK pathway begins with the activation of Raf kinase and is followed by the activation of MAP kinase (MEK) and mitogen activated protein kinase (MAPK). A variety of genes, including those required for cell cycle progression, are targets for MAPK. The Ras/MEK/MAPK pathway is also involved in the control of apoptosis, presumably by upregulating anti-apoptotic proteins such as bcl-2 or mcl-1 (Bonni, et. al., 1999, Science, 286:1358-1362).

Herpes Simplex Virus Type 2 (HSV-2) is a dual tropic virus that infects cells of the mucosal epithelium as well as cells of the nervous system. HSV-2 encodes a ribonucleotide reductase (RR) enzyme comprised of two subunits, referred to as the large and small subunits, encoded by the UL39 and UL40 genes, respectively. Within the large submit of HSV-2 RR (ICP10), resides a protein kinase domain termed ICP10PK whose sequence is known in the art. ICP10PK exhibits intrinsic protein kinase activity and has previously been shown to cause neoplastic transformation in a variety of cell types.

Viruses depend on cells for their replication and they can differenitially affect various signaling pathways. Herpes Simplex Virus Type 1 (HSV-1) and HSV-2 can trigger or counteract apoptosis in a cell-specific manner (Aubert et al., 1999, J. Virol., 73:2803-2813; Aubert et al., 1999, J. Virol., 73:10359-10370; Chou et al., 1992, Proc. Natl. Acad. Sci. USA, 89:3266-3270). Anti-apoptotic activity was ascribed to the HSV-1 and HSV-2 gene US3, and to the HSV-1 genes $\gamma_1 34.5$, US5, ICP27, and LAT (Aubert et al., 1999, J. Virol., 73:2803-2813; Chou et al., 1992, Proc. Natl. Acad. Sci. USA, 89:3266-3270). However, their exact mechanism of action and their activity in hippocampal neurons, if any, are still poorly understood.

There is a long felt need for treatment programs which arrest or alleviate neurological diseases where the diseases are caused, at least in part, by apoptosis of neuronal cells. The present invention satisfies this need.

BRIEF SUMMARY OF THE INVENTION

The invention includes a method of inhibiting neuronal apoptosis in a mammal. The method comprises administering to the mammal an apoptosis-inhibiting amount of an isolated nucleic acid encoding ICP10, or any mutant, variant, homolog, or fragment thereof having anti-apoptotic activity.

In a preferred embodiment of the invention, neuronal apoptosis is associated with a neurodegenerative disorder. In a further preferred embodiment, the neurodegenerative disorder is Alzheimer's disease (AD), amyotrophic lateral sclerosis (ALS), Down syndrome (DS), diabetic neuropathy, Parkinson's disease (PD), or Huntington disease (HD).

In another preferred embodiment, neuronal apoptosis is associated with an injury of the central or peripheral nervous system. In a further preferred embodiment, the injury is the result of stroke, cerebral ischemia, or chemical and/or physical trauma.

The invention also includes a method of inhibiting neuronal apoptosis in a mammal. The method comprises administering to the mammal an apoptosis-inhibiting inhibiting amount of the combination of an isolated nucleic acid encoding ICP10, or any mutant, variant, homolog, or fragment thereof having anti-apoptotic activity, and an isolated nucleic acid encoding bcl-2, or any mutant, variant, liomolog, or fragment thereof having anti-apoptotic activity.

In a preferred embodiment, the isolated nucleic acid encoding ICP10 and the isolated nucleic acid encoding bcl-2 are polycistronic.

The invention also includes a method of inhibiting neuronal apoptosis in a mammal. The method comprises administering to the mammal an apoptosis-inhibiting amount of a vector comprising a nucleic acid encoding ICP10, or any mutant, variant, homolog, or fragment thereof having anti-apoptotic activity.

In a preferred embodiment, the vector is a virus or a plasmid. In a further preferred embodiment, the virus is a herpesvirus, adenovirus, adeno associated virus, retrovirus, vaccinia virus, or canary pox virus. In yet a further preferred embodiment, the herpesvirus is HSV-2. In another embodiment, the HSV-2 comprises a mutation that renders the HSV-2 replication-defective. Further preferred, the mutation eliminates the ribonucleotide reductase domain of ICP10. In still another preferred embodiment, the ribonucleotide reductase domain is replaced with nucleic acid selected from the group consisting of a nucleic acid encoding LacZ and a nucleic acid encoding bcl-2, or any mutant, variant, homolog, or fragment thereof having anti-apoptotic activity.

The invention includes a method of inhibiting neuronal apoptosis in a mammal. The method comprises administering to the mammal an apoptosis-inhibiting amount of a polypeptide encoded by a nucleic acid encoding ICP10, or any mutant, variant, homolog, or fragment thereof having anti-apoptotic activity.

In a preferred embodiment of the invention, the ICP10 polypeptide is fused to a polypeptide encoded by a nucleic acid encoding bcl-2, or any mutant, variant, homolog, or fragment thereof having anti-apoptotic activity.

In another preferred embodiment of the invention, neuronal apoptosis is associated with a neurodegenerative disorder. Further preferred, the neurodegenerative disorder is Alzheimer's disease (AD), amyotrophic lateral sclerosis (ALS), Down syndrome (DS), diabetic neuropathy, Parkinson's disease (PD), or Huntington disease (HD).

In another preferred embodiment, neuronal apoptosis is associated with an injury of the central or peripheral nervous system. In a further preferred embodiment, the injury is the result of stroke, cerebral ischemia, or chemical and/or physical trauma.

The invention includes a method of inhibiting neuronal apoptosis in a mammal. The method comprises administering to the mammal an apoptosis-inhibiting amount of the combination of a polypeptide encoded by a nucleic acid encoding ICP10, or any mutant, variant, homolog, or fragment thereof having apoptotic activity and a polypeptide encoded by a nucleic acid encoding bcl-2, or any mutant, variant, homolog, or fragment thereof having apoptotic activity.

The invention also includes a method of inhibiting apoptosis in a mammal. The method comprises administering to the mammal an apoptosis-inhibiting amount of an isolated nucleic acid encoding ICP10, or any mutant, variant, homolog, or fragment thereof having anti-apoptotic activity.

The invention includes a method of inhibiting apoptosis in a mammal, wherein the method comprises administering to the mammal an apoptosis-inhibiting amount of the combination of an isolated nucleic acid encoding ICP10, or any mutant, variant, homolog, or fragment thereof having anti-apoptotic activity, and an isolated nucleic acid encoding bcl-2, or any mutant, variant, homolog, or fragment thereof having anti-apoptotic activity.

The invention also includes a method of inhibiting apoptosis in a mammal, wherein the method comprises administering to the mammal an apoptosis-inhibiting amount of a vector comprising a nucleic acid encoding ICP10, or any mutant, variant, homolog, or fragment thereof having anti-apoptotic activity.

The invention includes a method of inhibiting apoptosis in a mammal, wherein the method comprising administering to the mammal an apoptosis-inhibiting amount of a polypeptide encoded by a nucleic acid encoding ICP10, or any mutant, variant, homolog, or fragment thereof having anti-apoptotic activity.

The invention also includes a method of inhibiting apoptosis in a mammal, wherein the method comprises administering to the mammal an apoptosis-inhibiting amount of a polypeptide encoded by a nucleic acid encoding ICP10, or any mutant, variant, homolog, or fragment thereof having anti-apoptotic activity.

In a preferred embodiment of the invention, the polypeptide is fused to a polypeptide encoded by a nucleic acid encoding bcl-2, or any mutant, variant, homolog, or fragment thereof having anti-apoptotic activity.

The invention includes a composition comprising a fusion polypeptide, wherein the fusion polypeptide comprises a portion of ICP10 polypeptide and a portion of a bcl-2 polypeptide. The composition further comprises a pharmaceutically acceptable carrier therefor.

BRIEF DESCRIPTION OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown.

In the drawings:

FIGS. 6A and 6D), cells labeled with the neuron-specific PE-conjugated TUJ1 (class III beta tubulin) antibody (FIGS. 6B and 6E), and label co-localization (FIGS. 6C and 6F) are shown.

FIGS. 14A through 14C is a series of images of photomicrographs depicting the morphology of Ts16 hippocampal neurons. Ts16 mouse hippocampal neurons were grown and transfected with pJW17, pJHL15, or remained non-transfected (FIGS. 14A, 14B, and 14C, respectively). Micrographs were taken by using phase-contrast microscopy at 72 hours post-transfection (five days in vitro).

DETAILED DESCRIPTION OF THE INVENTION

Figure 1A:
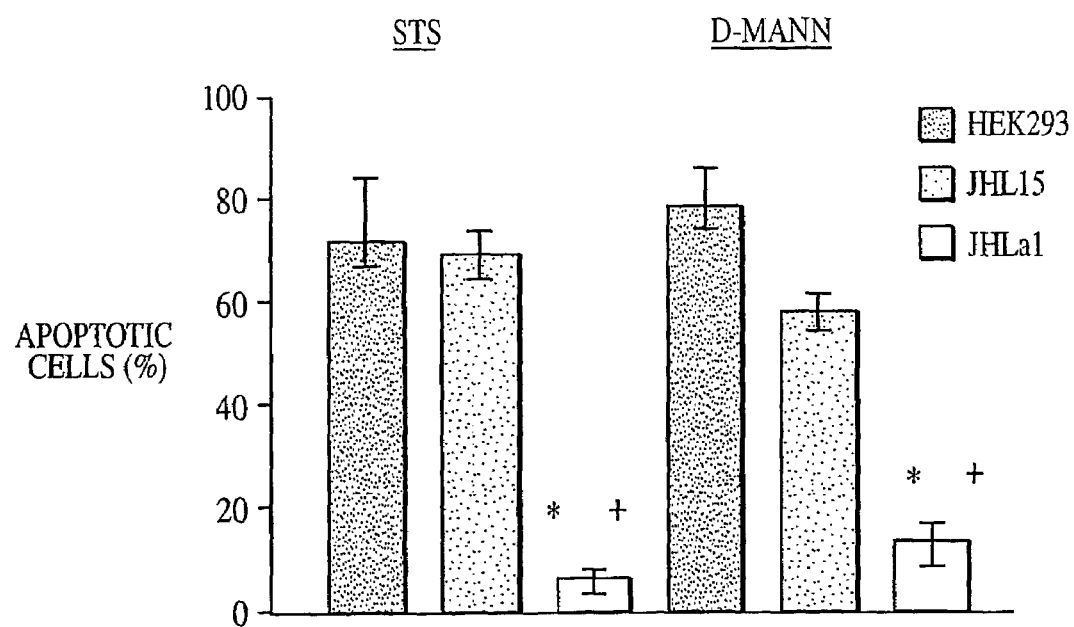
FIG. 1A is a graph depicting the apoptotic index of HEK293, JHL15, and JHLA1 cells treated with staurosporine (STS) and D-mannitol (D-Mann).

The invention relates to the discovery of the anti-apoptotic activity of HSV-2 ICP10PK and its use as an inhibitor of apoptosis of neuronal (as well as non-neuronal) cells in a mammal, including mammals suffering from neurodegenerative disorders and acute diseases involving neuronal degeneration. The invention discloses a neuroprotective role for ICP10, based on its ability to protect neurons from apoptosis induced by a variety of stimuli.

As disclosed herein, the PK domain of ICP10 (ICP10PK) inhibits apoptosis, as characterized by a reduction in the number of TdT-mediated dUTP nick end labeled (TUNEL)-positive cells, inhibition of DNA fragmentation, and inhibition of cellular morphologies characteristic of apoptosis. The anti-apoptotic activity of ICP10PK is shown herein to be effective against caspase-3-dependent apoptosis and is shown to involve activation of the MEK/MAPK pathway. ICP10PK blocks apoptosis induced by various chemical apoptotic inducers, including staurosporine (STS) and D-mannitol (D-Mann), as well as growth factor withdrawal, virus-induced apoptosis and apoptosis resulting from genetic defects.

Useful in the invention is an isolated nucleic acid encoding HSV-2 ICP10 (SEQ ID NO:1). The HSV-2 ICP10 gene (GeneBank No. M12700) is described in U.S. Pat. Nos.

6,013,265, 6,054,131, and 6,207,168, each of which is incorporated herein in their entirety.

In some aspects of the invention, mutants variants, homologs, or fragments of the isolated nucleic acid encoding ICP10 are useful. As disclosed herein, fragments of the isolated nucleic acid which encode only the PK domain of ICP10 arc useful in the invention. In one example, the ribonucleotide reductase (RR) domain is deleted from ICP10. Elimination of this domain is useful in that the resulting mutant is rendered non-virulent while it retains anti-apoptotic activity and the viral RR will not interfere with cellular processes governed by the RR encoded by the cell. Fragments of the nucleic acid encoding ICP10 can be generated by standard molecular biology procedures known in the art, for example in Sambrook et al. (1989, Molecular Cloning: A Laboratory Manual, Cold Spring Harbor Laboratory, New York), in Ausubel et al. (1997, Current Protocols in Molecular Biology, John Wiley & Sons, New York), and in Gerhardt et al. (eds., 1994, Methods for General and Molecular Bacteriology, American Society for Microbiology, Washington, D.C.). Further, the anti-apoptotic activity of ICP10 can be tested in cultured cells using the methods described in the examples herein.

Assays that measure induction of apoptosis in cells in vitro and ex vivo are described and used herein. These assays include TUNEL, DNA fragmentation assay, cell viability counts, HOECHST staining, and Western blots to measure inhibition of caspase activation and PARP cleavage.

Also useful in the invention is a vector comprising the nucleic acid encoding ICP10. Given the neurotropism of HSV-2, this virus serves as a useful vector for delivery of ICP10 to neurons. Particularly useful in the invention, is an ICP10-encoding HSV-2 vector wherein the RR domain of ICP10 has been deleted (ICP10deltaRR), thereby rendering the virus replication-defective but retaining the anti-apoptotic activity of the PK domain of ICP10. Other viral and non-viral vectors encoding ICP10 may also be useful in the invention. For example, retrovirus vectors expressing ICP10 or ICP10PK can be used to stably infect neuronal stem cells useful in ex vivo gene therapy. Other viral vectors including, but not limited to, adenovirus, vaccinia virus, canary pox virus, and adeno associated virus are useful for delivery and expression of ICP10 or ICP10PK using in vivo gene therapy.

Vectors encoding ICP10 can be constructed by standard molecular biology techniques. An HSV-2 vector, ICP10deltaRR, wherein the RR domain of ICP10 was replaced with a nucleic acid encoding LacZ was constructed previously (U.S. Pat. Nos. 5,965,356, 6,013,265, 6,054,131, and 6,207,168). Construction of ICP10deltaRR is described further in the examples presented herein. Other HSV-2 vectors encoding mutants, variants, homologs, or fragments of ICP10 can be constructed by similar methods.

Also useful in the invention is an ICP10 nucleic acid sequence operably linked to a promoter regulator) sequence that facilitates expression of ICP10. It may be particularly useful to link the nucleic acid encoding ICP10 to a tissue specific or an inducible promoter. Because the invention relates to the expression of ICP10 in neuronal cells, neuron-specific promoters will be useful to induce the expression of ICP10 specifically in these cells. Promoters useful to the invention are specific for neuronal cells; these include the neuron-specific enolase (NSE) and tyrosine hydroxylase (TH) promoters, TH-NFH (neurofilament heavy subunit) chimeric promoter, and the golli promoter; each of these promoters is described in detail below. Endogenous mammalian NSE is expressed in essentially all neurons, beginning during development at the time of synaptogenesis; its activity increases at a steady rate into adulthood when amounts of this protein can reach levels of up to 1% of the total cell protein (Marangos et al., 1987, Ann. Rev. Neurosci., 60:269-295). The pattern of expression of this promoter makes it a good candidate for conferring long-term expression of foreign genes on adult neurons following delivery by a viral vector. The TH-NFH promoter supports long-term gene expression in striatal neurons (Wang et al., 2001, Biotechniques, 31:204-212). Golli products of the myelin basic protein (MBP) gene have been found to be expressed in neurons during postnatal and embryonic development including Cajal-Retzius and cortical subplate neurons. Moreover, golli expression occurrs in other cortical neurons including neurons from cortical layer V and the hippocampus (Pribyl et al., 1996, J. Comp. Neurol., 374:342-353; Pribyl et al., 1993, Proc. Natl. Acad. Sci. USA, 90:10695-10699). Consequently, the golli promoter may be useful for driving transgene expression in selected neuronal populations.

Viral promoters including the HSV latency associated transcript (LAT) promoter, the Moloney murine leukemia virus (Mo-MLV) long terminal repeat (LTR), and the human cytomegalovirus (HCMV) immediate early (IE) promoter may also by useful. The LAT promoter includes elements both upstream and downstream of the start site of the minor LAT mRNA from which the intranuclear LATs are derived. Promoter elements referred to as LAP2 (latency active promoter 2) and LAP1 (contains neuronal responsive elements) are independently capable of expressing LAT during viral latency in sensory ganglia. The transgene can be placed downstream of LAP1 near the start of the LAT mRNA or downstream of both promoters within the LAT intron. Stable transgene expression has been achieved in sensory ganglia, but expression in CNS neurons was less vigorous (Fink et al., 1997, Nature Med, 3:357-359). The LTR of Mo-MLV has been used with HSV vectors to yield stable expression of the LacZ gene in sensory neurons and extended expression in motor neurons of the hypoglossal nucleus (Dobson et al., 1990, Neuron, 5:353-360). The HCMV IE promoter is a very strong constitutive promoter that is active in a wide variety of cell types including CNS neurons both in vitro (Johnson et al., 1992, Mol. Brain Res., 12:95-102) and in vivo (Wood et al., 1994, Exp. Neurol., 130:127-140). The vectors described above may also comprise such promoters operably linked to the ICP10 nucleic acid.

Also useful to the invention is an isolated ICP10 polypeptide or a mutant, variant, homolog, or fragment thereof having the anti-apoptotic activity of ICP10, as described herein. As described above, fragments of ICP10 in which the RR domain has been deleted are shown herein to be useful in the invention.

ICP10 polypeptides or mutant, homolog, or fragments thereof can be delivered using standard methods of peptide delivery known in the art. Specifically, the use of liposomes may be useful for ICP10 peptide delivery.

Also useful in the invention is an isolated nucleic acid encoding bcl-2 (GenBank No. M14745) in combination with an isolated nucleic acid encoding ICP10. Similar to ICP10, bcl-2 has anti-apoptotic activity. However, ICP10 and bcl-2 inhibit apoptosis via distinct pathways. ICP10PK acts as a growth factor receptor, signalling at the cellular membrane via Raf, MEK, and ERK, and bcl-2 appears to function much further downstream in an apoptotic inhibition pathway. In addition, the mechanism of apoptosis inhibition appears to be different. Whereas ICP10PK blocks cytochrome c release from the mitochondria by activating a protein other than bcl-2 (BAG-1) which ultimately leads to inhibition of caspase activation. In contrast, bcl-2 appears to function far downstream (directly at the level of the mitochondria) to inhibit cytochrome c release. Therefore, ICP10PK functions to activate downstream targets other than bcl-2 and has a significantly broader apoptotic activity than bcl-2. Since these proteins function through apparently distinct pathways, the use of both to inhibit apoptosis is likely to have a synergistic effect.

A number of ICP10 and bel-2 nucleic acid combinations are useful in the invention. For example an isolated nucleic acid encoding ICP10 may be delivered to a neuron in combination with an isolated nucleic acid encoding bcl-2. Alternatively, the two nucleic acids may be linked using standard molecular biology techniques and delivered as a single fused nucleic acid molecule. Further, fragments of either molecule may be delivered, wherein each fragment retains biological activity of the respective protein encoded thereby.

The biological activity of ICP10PK differs from that of bcl-2 in that, although both inhibit apoptosis. ICP10PK functions at the beginning of the apoptotic signaling cascade and results in the activation of end points other than bcl-2, such as bag-1, and bcl-2 functions at the end of the cascade, inhibiting cytochrome c release from the mitochondria. Thus, the biological activity of ICP10PK is defined as the ability to inhibit apoptosis in a cell at the beginning of the apoptotic signaling cascade. In contrast, the biological activity of bcl-2 is defined as the ability to inhibit apoptosis by directly blocking cytochrome c release from the mitochondria.

The bcl-2 family of proteins acts at the mitochondrial level to prevent mitochondrial dysfunctions such as membrane potential loss and the membrane permeability transition, which allows the release of the mitochondrial apoptosis-inducing factor (AIF) and cytochrome c, a process that initiates the apoptotic cascade. Moreover, bcl-2 family members sequester the proforms of caspases, inhibiting their activation. Conversely, bcl-2 has a broad anti-apoptotic activity (Tsujimoto, 1998, In: Apoptosis: Mechanisms and Role in Disease, 137-155). There are, however, pathways to apoptosis that are insensitive to bcl-2, such as apoptosis induced by activation of CD95 and TNF receptors (Strasser et al., 1995, EMBO J., 14:6136-6147). Moreover, bcl-2 is overexpressed in AD brains (Kitamura et al., 1998, Brain Res., 780:260-269), a process which cannot, however, circumvent neuronal death. Bcl-2 does not protect against motoneuron degeneration in wobbler and progressive motor neuropathy (Sagot et al., 1995, J. Neurosci., 15.:7727-7733), which suggests that bcl-2 alone would not be sufficient for treatment of neurodegenerative disorders.

By contrast, ICP10PK activates cellular signaling pathways such as Ras/MEK/MAPK which are involved in survival as well as in maintaining a normal neuronal physiology. As such, Ras/MEK/MAPK promotes survival by transcription-independent (phosphorylation of pro-apoptotic protein Bad by Raf which changes its status from pro- to anti-apoptotic) or transcription-dependent (increased transcription of anti-apoptotic proteins, including bcl-2 and bag-1) mechanisms (Kaplan et al., 2000, Curr. Opin. Neurobiol., 10:381-391). Besides direct activation of the cell protein synthesis machinery, MAPKs are also involved in modulation of ion-channel function (Grewal et al., 1999, Curr. Opin. Neurobiol., 9:544-553) and phosphorylation of synapsin I (Jovanovic et al., 1996, Proc. Natl. Acad. Sci. USA, 93:3679-3683) and these functions may represent mechanisms by which neurotrophins exert rapid effects on neurotransmission. MAPKs are required for hippocampal long term potentiation (LTP) (English et al., 1997, J. Biol. Chem., 272:19103-19106) which represents the molecular mechanism that underlies learning and memory. Compelling evidence for a MAPK-dependent role in learning and memory has come from rodent behavioral studies, where behavioral performance was associated with increased MAPK activity, and inhibition of MAPK signaling specifically impaired learning (Blum et al., 1999, J. Neurosci., 19:3535-3544; Berman et al., 1998, J. Neurosci., 18:10037-10044; Atkins et al., 1998, Nat. Neurosci., 1:602-609). Taken together, these data provide strong evidence that the Ras/MEK/MAPK pathway, in addition to conducting survival signals, may also be required for both synaptic plasticity and learning and memory.

Also useful in the invention are vectors comprising nucleic acids encoding ICP10 and bcl-2. The nucleic acids may be present within separate vectors or within the same vector. When the nucleic acids are within the same vector, the nucleic acids may be polycistronic such that their expression is linked to one another or they may be expressed independently from one another. Many vectors may be useful for delivering the combination of ICP10 and bcl-2 to cells in a mammal. In a preferred aspect of the invention, a recombinant HSV-2 vector in which the RR domain of ICP10 has been replaced with the nucleic acid encoding bcl-2 is used to deliver ICP10 and bcl-2 to neuronal cells. One version of this virus will express an ICP10-bcl-2 fusion protein, whereas another version will express the two proteins separately. Construction of these viruses is described in the examples section herein.

In the methods of the invention, ICP10 may be delivered to neuronal cells in the form of a nucleic acid expressing ICP10, preferably using vectors or liposomes, or it may be delivered to cells in the form of a polypeptide, or a fragment thereof. Thus, the use of ICP10 polypeptide (SEQ ID NO:2) and fragments thereof, including all mutants and variants having IPC10 biological activity as defined here, are included in the methods of the invention. ICP10 polypeptides can be easily generated using methods well known in the art described, for example, in Sambrook et al. (supra) and in Ausebel et al (supra). further, ICP10 mutants are described in U.S. Pat. Nos. 6,013,265, 6,054,131, and 6,207,168

Also useful in the methods of the invention is the use of a combination or ICP10 and bcl-2 polypeptides. The two proteins can be delivered independently or together as a fusion protein. An ICP10-bcl-2 fusion protein can be constricted using standard techniques known in the art wherein the nucleic acids encoding each protein are operably linked as described above. The combination of the ICP10 and bcl-2 polypeptides or fusion polypeptides may be delivered to neuronal cells by the methods described above for delivery of ICP10 protein alone.

ICP10 is shown herein to protect hippocampal neurons from death induced by withdrawal of neurotrophic support. Furthermore, ICP10 rescued mouse Ts16 cells, a naturally occurring model for DS, from apoptosis, demonstrating the anti-apoptotic activity of ICP10 specifically with respect to genetic defects associated with neurodegeneration. Given that many clinically-significant neurodegenerative disorders are characterized by neuronal apoptosis, the invention makes use of the anti-apoptotic activity of ICP10 to treat such disorders, including, but not limited to, AD, ALS, DS, PD, and HD. Notably, the therapeutic value of ICP10 for treatment of neurodegenerative disorders is further substantiated by the demonstration herein that peripheral administration using a viral vector effectively delivers ICP10 to the central nervous system (CNS). Thus, the data presented herein demonstrate the usefulness of ICP10 in inhibiting neuronal apoptosis, including that associated with neurodegenerative disorders.

The invention includes a method of inhibiting apoptosis of neuronal cells in a mammal. The method comprises administering to the mammal an apoptosis-inhibiting amount of an isolated nucleic acid encoding ICP10. The invention should be construed to include administration of alternative forms of ICP10 having anti-apoptotic activity, including mutants, variants, homologs, and fragments of ICP10. Specifically, fragments of ICP10 which retain the PK domain of ICP10 and thus retain the anti-apoptotic activity of ICP10 are useful for inhibiting cellular apoptosis, as disclosed herein. The anti-apoptotic activity of ICP10 maps to the PK domain (amino acids 1 to 411), and thus, fragments useful to the invention will comprise this domain.

The isolated nucleic acid encoding ICP10 can be administered to a mammal using a variety of methods. In a preferred embodiment of the invention, ICP10 is delivered using a vector. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, herpesvirus vectors, adenoviral vectors, adeno-associated virus vectors, retroviral vectors, and the like.

The present invention also provides for a method of inhibiting apoptosis using analogs of proteins or peptides encoded by ICP10. Analogs can differ from naturally occurring proteins or peptides by conservative amino acid sequence differences or by modifications which do not affect sequence, or by both.

For example, conservative amino acid changes may be made, which although they alter the primary sequence of the protein or peptide, do not normally alter its function. Conservative amino acid substitutions typically include substitutions within the following groups:
glycine, alanine;
valine, isoleucine, leucine;
aspartic acid, glutamic acid;
asparagine, glutamine;
serine, threonine;
lysine, arginine;
phenylalanine, tyrosine.

Modifications (which do not normally alter primary sequence) include in vivo, or in vitro chemical derivatization of polypeptides, e.g., acetylation, or carboxylation. The invention should be construed to include administration of modified ICP10 peptides including, but not limited to, peptides modified by glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. Also embraced is a method of inhibiting apoptosis comprising administration of ICP10 peptides which have phosphorylated amino acid residues, e.g., phosphotyrosine, phosphoserine, or phosphothreonine.

The invention further includes a method of inhibiting apoptosis by administering ICP10 polypeptides which have been modified using ordinary molecular biological techniques so as to improve their resistance to proteolytic degradation or to optimize solubility properties or to render them more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Pharmaceutical compositions comprising ICP10 nucleic acid, vectors comprising the same, or peptides encoded thereby, may be formulated and administered to a mammal for inhibition of apoptosis. Such compositions are now described.

The invention encompasses the preparation and use of pharmaceutical compositions comprising an ICP10 compound useful for inhibition of apoptosis as an active ingredient. Such a pharmaceutical composition may consist of the active ingredient alone, in a form suitable for administration to a subject, or the pharmaceutical composition may comprise the active ingredient and one or more pharmaceutically acceptable carriers, one or more additional ingredients, or some combination of these. The active ingredient may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which the active ingredient may be combined and which, following the combination, can be used to administer the active ingredient to a subject.

As used herein, the term "physiologically acceptable" ester or salt means an ester or salt form of the active ingredient which is compatible with any other ingredients of the pharmaceutical composition, which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient into association with a carrier or one or more other accessory ingredients, and then, if necessary or desirable, shaping or packaging the product into a desirable single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other primates, and other mammals.

Pharmaceutical compositions that are useful in the methods of the invention may be prepared, packaged, or sold in formulations suitable for parenteral, topical, pulmonary, intranasal, buccal, ophthalmic, intrathecal or another route of administration.

A pharmaceutical composition of the invention may be prepared, packaged, or sold in bulk, as a single unit dose, or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multi-dose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers. The formulations described herein as being useful for pulmonary delivery are also useful for intranasal delivery of a pharmaceutical composition of the invention.

Typically dosages of the compound of the invention which may be administered to an animal, preferably a human, range in amount from 1 microgram to about 100 grams for proteins and peptides, $10^3$ to $10^8$ plaque forming units for viruses, and 1 to 500 micrograms for DNA.

The compound may be administered to an animal as frequently as several times daily, or it may be administered less frequently, such as once a day, once a week, once every two weeks, once a month, or even less frequently, such as once every several months or even once a year or less. The frequency of the dose will be readily apparent to the skilled artisan and will depend upon any number of factors, such as, but not limited to, the type and severity of the disease being treated, the type and age of the animal, etc.

For example, treatment of AD, a chronic disease, may be performed as follows. ICP10deltaRR can be given by intranasal spraying, a non-invasive and widely accepted delivery route, although other routes of administration are possible. As stated above, $10^3$ to $10^8$ plaque forming units of ICP10deltaRR can be used for infection. Assuming that gene expression does not last more than 20 days, monthly re-exposure will be needed (or at least 10 exposures per year).

To treat an acute disease, such as stroke, ICP10delta RR can be administered as described above. Again assuming that gene expression does not last more than 20 days, re-exposure will only be needed 2 or 3 additional times (4 exposures total).

Also included in the invention is a method of inhibiting apoptosis of neuronal cells in a mammal by administering ICP10 in combination with bcl-2. Like ICP10, bcl-2 inhibits apoptosis; however, the mechanism of inhibition appears to be distinct from that ICP10. Thus, administration of ICP10 and bcl-2 will have a cumulative anti-apoptotic activity due to the ability of these two proteins to activate distinct survival pathways. The invention should be construed to include administration of ICP10 and bcl-2 nucleic acids, a vector comprising ICP10 and bcl-2 nucleic acids, and the ICP10 and bcl-2 polypeptides encoded thereby as well as pharmaceutical compositions comprising the same, as described herein. Fusion proteins comprising portions of ICP10 and bcl-2 are also considered in the invention, wherein the administration of the fusion protein or a nucleic acid encoding the fusion protein inhibits apoptosis in a tissue in a mammal. In additional embodiments, members of the bcl-2 family with anti-apoptotic activity that are not activated by ICP10PK may be useful for combination delivery. Specifically, these can be delivered as peptide cocktails, mixed DNA preparations, or other fusion proteins with ICP10 expressed by the ICP10deltaRR mutant virus, as two such genes could likely be incorporated into the virus.

In a preferred embodiment of the invention, ICP10 is used to inhibit neuronal apoptosis in a mammal suffering from a neurodegenerative disorder. Neurodegenerative diseases amenable to treatment with ICP10 include AD, ALS, DS, PD, and HD. Some examples of diseases which may be treated according to the methods of the invention are discussed herein. The invention should not be construed as being limited solely to these examples, as other neurodegenerative diseases which are at present unknown, once known, may also be treatable using the methods of the invention.

Examples of acute diseases that could be treated with ICP10PK include stroke, cerebral ischemia, chemical and/or physical trauma, and spinal cord injury. Patients suffering any of these injuries experience neuronal apoptosis and may be treated effectively with ICP10PK. These types of injuries require treatment within days, if not hours of the. injury and are excellent candidates for the anti-apoptotic use of ICP10PK. Thus, administration of ICP10PK is useful in inhibiting apoptosis in both the central nervous system as well as the peripheral nervous system, where it will be particularly effective in cases of spinal cord injury and diabetic neuropathy.

Preferred methods of ICP10 administration specifically for the purpose of inhibiting neuronal apoptosis in a mammal include intranasal administration and subcranial injection of a nucleic acid encoding ICP10, a vector comprising the same, or a polypeptide encoded thereby. The use of liposomes to deliver ICP10-encoding nucleic acids may also be useful in the invention.

In a preferred embodiment of the invention, ICP10 is administered using a mutant form of HSV-2, designated ICP10deltaRR, in which the ribonucleotide reductase domain of ICP10 is replaced with the gene encoding LacZ. The ICP10deltaRR virus is known in the art (Peng et al., 1996, Virology, 216:184-196; U.S. Pat. Nos. 5,965,356, 6,013,265, 6,045,131, and 6,207,168). LacZ-specific staining facilitates detection of cells that are infected with the mutant virus, and more specifically, cells that are expressing ICP10.

ICP10deltaRR can also have a deletion of the RR gene, without the addition of the LacZ gene. One could replace the LacZ gene with bcl-2 or any other gene of interest, for example, a growth factor.

The invention further includes a method of administering ICP10 in combination with bcl-2 to inhibit apoptosis of neurons in a mammal. As described in detail above, since ICP10 and bcl-2 inhibit apoptosis through distinct pathways, the combination of ICP10 and bcl-2 will have a cumulative effect. Inhibition of neuronal apoptosis may be achieved by administration of ICP10 and bcl-2 nucleic acids, a vector comprising ICP10 and bcl-2 nucleic acids, and the ICP10 and bcl-2 polypeptides encoded thereby, as well as pharmaceutical compositions comprising the same as described herein. Again, fusion proteins comprising portions of ICP10 and bcl-2 ale also considered in the invention, wherein the administration of the fusion protein or a nucleic acid encoding the fusion protein inhibits neuronal apoptosis in a mammal.

In a preferred embodiment, ICP10 and bcl-2 are administered in combination to inhibit neuronal apoptosis using an HSV-2 mutant virus in which the ribonucleotide reductase domain of ICP10 has been replaced with the bcl-2 gene. A mutant virus in which the RR domain of ICP10 is replaced with bcl-2 can be constructed as described in the examples presented herein.

Administration of ICP10, or ICP10 in combination with bcl-2 may also be useful for treatment of apoptosis in cells other than neurons. As disclosed herein, ICP10PK inhibits apoptosis in human kidney cells (JHLA1 cells). Thus, the invention may also be used to treat non-neuronal diseases which rely upon inhibition of apoptosis for their treatment.

Definitions

The articles "a" and "an" are used herein to refer to one or to more than one (i.e. to at least one) of the grammatical object of the article. By way of example, "an element" means one element or more than one element. "Plurality" means at least two.

As used herein, cells or tissue are "affected" by a disease or disorder if the cells or tissue have an altered phenotype relative to the same cells or tissue in a subject not afflicted with a disease or disorder.

As used herein, amino acids are represented by the full name thereof, by the three letter code corresponding thereto, or by the one-letter code corresponding thereto, as indicated in the following table:

| Full Name | Three-Letter Code | One-Letter Code |
| --- | --- | --- |
| Aspartic Acid | Asp | D |
| Glutamic Acid | Glu | E |
| Lysine | Lys | K |
| Arginine | Arg | R |
| Histidine | His | H |
| Tyrosine | Tyr | Y |
| Cysteine | Cys | C |
| Asparagine | Asn | N |
| Glutamine | Gln | Q |
| Serine | Ser | S |
| Threonine | Thr | T |
| Glycine | Gly | G |
| Alanine | Ala | A |
| Valine | Val | V |
| Leucine | Leu | L |
| Isoleucine | Ile | I |
| Methionine | Met | M |
| Proline | Pro | P |
| Phenylalanine | Phe | F |
| Tryptophan | Trp | W |

As used herein, the term "apoptosis" means a process by which a cell is affected in such a way that it begins the process of programmed cell death, which is characterized by the fragmentation of the cell into membrane-bound particles that are subsequently eliminated by the process of phagocytosis. Thus, "inhibition of apoptosis" means reducing or eliminating the apoptotic process in cells.

"Inappropriate apoptosis" of cells refers to apoptosis (i.e. programmed cell death) which occurs in cells of an animal at a rate different from the range of normal rates of apoptosis in cells of the same type in an animal of the same type which is not afflicted with a disease or disorder.

A "coding region" of a gene consists of the nucleotide residues of the coding strand of the gene and the nucleotides of the non-coding strand of the gene which are homologous with or complementary to, respectively, the coding region of an mRNA molecule which is produced by transcription of the gene.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a symptom of the disease or disorder, the frequency with which such a symptom is experienced by a patient, or both, are reduced.

"Encoding" refers to the inherent property of specific sequences of nucleotides in a polynucleotide, such as a gene, a cDNA, or mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

As used herein, a "functional" biological molecule is a biological molecule in a form in which it exhibits a property by which it is characterized. A functional enzyme, for example, is one which exhibits the characteristic catalytic activity by which the enzyme is characterized.

"Homologous" as used herein, refers to the subunit sequence similarity between two polymeric molecules, e.g., between two nucleic acid molecules, e.g., two DNA molecules or two RNA molecules, or between two polypeptide molecules. When a subunit position in both of the two molecules is occupied by the same monomeric subunit, e.g., if a position in each of two DNA molecules is occupied by adenine, then they are homologous at that position. The homology between two sequences is a direct function of the number of matching or homologous positions, e.g., if half (e.g., five positions in a polymer ten subunits in length) of the positions in two compound sequences are homologous then the two sequences are 50% homologous, if 90% of the positions, e.g., 9 of 10, are matched or homologous, the two sequences share 90% homology. By way of example, the DNA sequences 3'ATTGCC5' and 3'TATGGC share 50% homology.

As used herein, "homology" is used synonymously with "identity".

Percent identity of one polynucleotide or polypeptide with respect to another polynucleotide or polypeptide may be determined using any available algorithm, such as the BLAST program.

To determine the percent identity of two amino acid sequences or of two nucleic acids, the sequences are aligned for optimal comparison purposes (e.g. gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid or nucleotide residue as the corresponding position in the second sequence, then the molecules are identical at that position. The percent identity between the two sequences is a function of the number of identical positions shared by the sequences (i.e., percent identity is equal to the number of identical positions divided by the total number of positions (e.g., overlapping positions) multiplied by 100). In one embodiment the two sequences are the same length, at least after introducing gaps into one or both sequences.

Determination of percent identity between two sequences can be accomplished using a number of mathematical algorithm. A preferred, non-limiting example of a mathematical algorithm used for comparison of two sequences is the algorithm of Karlin and Altschul (1990) *Proc. Natl. Acad. Sci. USA* 87:2264-2268, modified as in Karlin and Altschul (1993) *Proc. Natl. Acad. Sci. USA* 90:5873-5877. Such an algorithm is incorporated into the NBLAST and XBLAST programs of Altschul et al. (1990) *J. Mol. Biol.* 215:403-410. BLAST nucleotide searches can be performed with the NBLAST program, score=100, wordlength=12 to obtain nucleotide sequences homologous to a nucleic acid molecules of the invention. BLAST protein searches can be performed with the XBLAST program, score=50, wordlength=3 to obtain amino acid sequences homologous to a protein molecules of the invention. To obtain gapped alignments for comparison purposes, gapped BLAST analysis can be used as described in Altschul et al. (1997) *Nucleic Acids Res.* 25:3389-3402. Alternatively, PSI-Blast can be used to perform an iterated search which detects distant relationships between molecules. Id. When using BLAST, gapped BLAST, and PSI-Blast analyses, default parameters of the respective programs (e.g., XBLAST and NBLAST) can be used. See http://www.ncbi.nlm.nih.gov. Another preferred, non-limiting example of a mathematical algorithm used for comparison of sequences is the algorithm of Myers and Miller. (1988) *CABIOS* 4:11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson and Lipman (1988) *Proc. Natl. Acad. Sci. USA* 85:2444-2448. When using the FASTA algorithm for comparing nucleotide or amino acid sequences, a PAM120 weight residue table can, for example, be used with a k-tuple value of 2.

The percent identity between two sequences can be determined using techniques similar to those described above, with or without allowing gaps. In calculating percent identity, only exact matches are counted.

An "isolated nucleic acid" refers to a nucleic acid segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to nucleic acids which have been substantially purified from other components which naturally accompany the nucleic acid, e.g., RNA or DNA or proteins, which naturally accompany it in the cell. The term therefore includes, for example, a recombinant DNA which is incorporated into a vector, into an autonomously replicating plasmid or virus, or into the genomic DNA of a prokaryote or eukaryote, or which exists as a separate molecule (e.g, as a cDNA or a genomic or EDNA fragment produced by PCR or restriction enzyme digestion) independent of other sequences. It also includes a recombinant DNA which is part of a hybrid gene encoding additional polypeptide sequence.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

By describing two polynucleotides as "operably linked" is meant that a single-stranded or double-stranded nucleic acid moiety comprises the two polynucleotide arranged within the nucleic acid moiety in such a manner that at least one of the two polynucleotides is able to exert a physiological effect by which it is characterized upon the other. By way of example, a promoter operably linked to the coding region of a gene is able to promote transcription of the coding region.

The term "nucleic acid" typically refers to large polynucleotides.

The term "oligonucleotide" typically refers to short polynucleotides, generally no greater than about 50 nucleotides. It will be understood that when a nucleotide sequence is represented by a DNA sequence (i.e., A, T, G, C), this also includes an RNA sequence (i.e., A, U, G, C) in which "U" replaces "T."

Conventional notation is used herein to describe polynucleotide sequences: the left-hand end of a single-stranded polynucleotide sequence is the 5'-end; the left-hand direction of a double-stranded polynucleotide sequence is referred to as the 5'-direction.

The direction of 5' to 3' addition of nucleotides to nascent RNA transcripts is referred to as the transcription direction. The DNA strand having the same sequence as an mRNA is referred to as the "coding strand"; sequences on the DNA strand which are located 5' to a reference point on the DNA are referred to as "upstream sequences"; sequences on the DNA strand which are 3' to a reference point on the DNA are referred to as "downstream sequences."

"Polypeptide" refers to a polymer composed of amino acid residues, related naturally occurring structural variants, and synthetic non-naturally occurring analogs thereof linked via peptide bonds, related naturally occurring structural variants, and synthetic non-naturally occurring analogs thereof. Synthetic polypeptides can be synthesized, for example, using an automated polypeptide synthesizer.

The term "protein" typically refers to large polypeptides.

The term "peptide" typically refers to short polypeptides.

Conventional notation is used herein to portray polypeptide sequences: the left-hand end of a polypeptide sequence is the amino-terminus; the right-hand end of a polypeptide sequence is the carboxyl-terminus.

As used herein, the term "promoter/regulatory sequence" means a nucleic acid sequence which is required for expression of a gene product operably linked to the promoter/regulator sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

An "inducible" promoter is a nucleotide sequence which, when operably linked with a polynucleotide which encodes or specifies a gene product, causes the gene product to be produced in a living cell substantially only when an inducer which corresponds to the promoter is present in the cell.

A "tissue-specific" promoter is a nucleotide sequence which, when operably linked with a polynucleotide which encodes or specifies a gene product, causes the gene product to be produced in a living cell substantially only if the cell is a cell of the tissue type corresponding to the promoter.

A "vector" is a composition of matter which comprises an isolated nucleic acid and which can be used to deliver the isolated nucleic acid to the interior of a cell.

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

HSV-2 ICP10PK Inhibits Apoptosis

The data herein demonstrate a neuroprotective role for ICP10PK expressed by a viral or expression vector. ICP10PK protects cells from apoptosis induced by virus, growth factor or genetic defects. Also, it is demonstrated that ICP10PK activates the Ras/MEK/MAPK pathway.

The materials and methods used in the experiments presented in this example are now described.

Cells

Vero (African green monkey kidney cells) were obtained from ATCC and grown in Minimum Essential Medium (MEM) with 10% fetal bovine serum (FBS) and antibiotics. HEK293 (human embryonic kidney) cells were grown in Dulbecco's Modified Eagle's Medium (DMEM) with 10% FBS, 1 mM sodium pyruvate, 0.1 mM non-essential amino acids, and antibiotics. The cell line JHLA1 was established from HEK293 cells by transfection with an ICP10 expression vector and clone selection with G418, and the cell line JHL15 was similarly constructed using a vector which expresses the transmembrane deleted mutant of ICP10, p139™, which is PK negative, as described (Smith et al. 1994, Virology, 200: 598-612).

Primary hippocampal cultures were produced from E17-E18 rats using a procedure previously described (Arcava, et al. 1987, FEBS Lett., 229:63-70). Briefly, minced fetal hippocampi were incubated with 0.25% trypsin for 30 minutes at 36° C. followed by dissociation of neurons in MEM supplemented with 10% FBS, 10% horse serum, 2 mM glutamine, and 20 microgram/ml DNase II, using a sterile Pasteur pipette. Neurons were plated at approximately 750,000 cells per 35 mm dish on glass coverslips pre-coated with poly-L-lysine and incubated at 36° C., 10% $CO_2$. At 24 hours, media was replaced with MEM supplemented with 10% horse serum and 2 mM glutamine, and the cultures were returned to a 36 degrees C., 10% $CO_2$ incubator. The results presented in this example were obtained using neurons at day 6 after plating.

Rat pheochromocytoma (PC12) cells were obtained from ATCC and were cultured in DMEM-F12 (Gibco-BRL) with 10% FBS, 0.36% D-glucose (Sigmna), 0.21% sodium bicarbonate, 0.009% gentamycin and 100 ng/ml nerve growth factor (NGF) (Roche Molecular Biochemicals). Generation of trisomic mice and karyotyping were previously described (Bambrick et al., 1999, J. Neurochem, 72:1769-1772). Primary hippocampal cultures from embryonic day 16 (E16) euploid and Ts16 mouse fetuses were established and grown as previously described (Bambrick et al., 1999, J. Neurochem, 72:1769-1772) on glass coverslips etched with a grid of 175×175 micrometers squares (CELLocate; Eppendorf, Madison, Wis.) in MEM with B27 supplement (Gibco) which contains optimized concentrations of neuron survival factors. For each Ts 16 fetus, an euploid fetus from the same litter was used.

The Ts16 mouse is considered to be a model of Down's syndrome (DS; trisomy 21). Ts16, as well as Ts21, are genetic defects believed to confer increased vulnerability to neurodegeneration (Coyle et al., 1988, Trends Neurosci., 11:390-394). Cultured hippocampal neurons from the Ts16 mouse exhibit increased cell death relative to littermate euploid cells, even in the presence of adequate trophic support (Bambrick et al., 1999, J. Neurochem., 72:1769-1772). To examine whether ICP10PK can promote survival in this system, primary hippocampal cultures from Ts16 mice (established as described in Bambrick et al., 1999, J. Neurochem. 72:1769-1772) were transfected with pJW17 or pJHL15 at 2 days in culture and maintained in B27-supplemented medium for the duration of the experiment.

Viruses

HSV-2 (strain G) and HSV-1 (strain F) were used throughout these studies (Ejercito et al., 1968, J. Gen. Virol, 2:357-364).

The HSV-2 ICP10deltaRR mutant was obtained using HSV-2 (G) by replacing the RR domain of ICP10 with the lacZ gene. The plasmid used for insertion of lacZ was previously described (Luo et al., 1992, J. Biol. Chem., 267:9645-9653). The construction of the ICP10deltaRR mutant virus was reported elsewhere (Peng et al., 1996, Virology, 216:184-196; Smith et al., 1998, J. Virol., 72:9131-9141). Briefly, BamHIE and T fragments from TP101 plasmid were replaced with a 1.8 kb SaII/BgIII fragment from plasmid pJHLA9 (Peng et al., 1996, Virology, 216:184-196), containing ICP10 with a deletion in the PK domain. A 10 kb HindIII/EcoRI fragment from the resulting plasmid (containing ICP10deltaPK sequence flanked by 4 and 2.8 kb HSV-2 DNA sequences at the 5' and 3' ends, respectively) was introduced into ICP10deltaRR. The recombinant virus such as obtained was selected by staining with X-gal (Boehringer Mannheim). ICP10deltaPK formed white plaques on a background of blue plaques. White plaques were picked and ICP10deltaPK virus stock was obtained by growing the virus in Vero cells with MEM, 10% FBS. Virus titers were determined by plaque assay as described (Aurelian, 1992, In: Clinical Virology Manual, $2^{nd}$ ed, Elseviers Science Publishers, New York, N.Y.). For viral replication kinetic determination (single step growth curves), primary cultures of rat hippocampal neurons at day 6 after plating were infected at a multiplicity of infection of 10 (MOI=10). After an adsorption phase of 1 hour, virus was removed and the initial media (MEM, 10% horse serum, 2 mM glutamine) was added to the neurons, followed by incubation at 36 degrees C., 10% $CO_2$, At the indicated times after infection, cells were collected by gentle scraping and centrifuged. The resulting pellet was re-suspended in 1 ml of supernatant. Seven cycles of freezing and thawing were performed before determining the viral titers. Titers were expressed in plaque forming units (PFU) per ml (PFU/ml). Single step growth curves were obtained by plotting titer versus time on a logarithmic axis.

Antibodies

The following antibodies were used in these studies: anti-GFAP (glial fibrillary acidic protein) and anti-GalC (galactocerebroside) antibodies were part of the Neural Cell Typing Set for Identification and Typing of Neural Cells (neurons, astrocytes, oligodendrocytes; Roche Molecular Biochemicals, Indianapolis, Ind.); anti-tubulin J (P. Yarowsky, University of Maryland, Baltimore); p-Erk (P-MAPK), which recognizes both phosphorylated forms of Erk (MAPK) enzyme (p42 and p44) (Promega, Madison, Wis.); anti-PARP (Roche Molecular Diagnostics, Indianapolis, Ind.) caspase-3 antibody (Santa Cruz Biotechnology, Santa Cruz, Calif.).

Treatment with Apoptosis Inducers

Apoptosis was induced in HEI293 and JHLA1 cells using staurosporine (STS; Calbiochem, San Diego, Calif.) and D-manritol (D-Mann; Sigma, St. Louis, Mo.). Cells were plated in 6-well plates on glass coverslips or in flasks and allowed to grow for 24 hours at 37° C. in DMEM with 10% FBS, 1 mM sodium pyruvate, 0.1 mM non-essential amino acids, and antibiotics. At 24 hours after plating, media was removed by aspiration, and appropriate dilutions of apoptotic inducers (STS 250 nM, D-Mann 300 mM) were added to the cells for various times indicated in the text. All dilutions were made in cell growth media described above containing 1% FBS. At the indicated times after treatment, cells were processed for TUNEL or harvested for DNA extraction or Western blot assay.

TUNEL (TdT-Mediated dUTP Nick End Labeling)

In situ analysis of apoptosis was performed using In Situ Cell Death Detection Kit (Roche Molecular Biochemicals, Indianapolis, Ind.) according to the manufacturer's instructions. Briefly, infected/treated or non-infected/non-treated cells were fixed with 4% paraformaldehyde (PFA) in PBS (pH=7.4) for 30 minutes at room temperature followed by permiabilization of cells in 0.1% Triton X-100 (in 0.1% sodium citrate) for 2 minutes on ice. DNA breaks were labeled by addition of terminal deoxynucleotidyl transferase (TdT) and nucleotide mixture (containing dUTP-fluorescein conjugated) and incubation for 60 minutes at 37° C. Coverslips were mounted in PBS/glycerol, and cells were analyzed by fluorescence microscopy. After extensive washes in PBS, cells were incubated for 30 minutes at 37° C. with an anti-fluorescein antibody conjugated with alkaline phosphatase (AP). Chromogenic reaction was carried out by adding AP substrate solution (NBT/BCIP in 0.1 M Tris-HCl pH=9.5, 0.05 M $MCl_2$, 0.1M NaCl, and 1 mM levamisole) and incubation for 10 minutes at room temperature. Coverslips were mounted in PBS/glycerol and analyzed by light microscopy. Apoptotic cells (characterized by a dark precipitate) and non-apoptotic cells (diffuse, light staining) were counted in at least five randomly chose microscopic fields (containing at least 250 cells). The percentage of mock-infected neurons undergoing apoptosis (between 4 and 5%) was subtracted from each average.

Apoptotic index refers to the average percentage of TUNEL-positive cells±SEM4.

Double labeling TUNEL/Neuronal Markers

Infected or non-infected hippocampal cultures were fixed with 4% PFA in PBS (pH=7.4) followed by permeabilization in 0.1% Triton X-100 (in 0.1% sodium citrate). Cells were incubated with TdT and nucleotide mixture (containing dUTP-fluorescein conjugated) for 1 hour at 37° C., followed by immunostaining with appropriate neuronal markers (anti-tubulin beta, anti-GFAP, anti-GalC). Signal was detected by incubating the cells with anti-mouse Ig conjugated to phycoerythrine (1:50 dilution) for 30 minutes at room temperature. Coverslips were mounted in PBS/glycerol and analyzed by fluorescence microscopy (Carl Zeiss microscope) using the appropriate filters.

DNA Fragmentation Assay

HEK293, JHLA1 and JHL15 cells treated or not treated with apoptotic inducers were collected by gentle scraping at 24 hours post-treatment/infection. DNA was extracted using Puregene DNA Isolation Kit (Gentra Systems, Minneapolis, Minn.) according to the manufacturer's instructions. After spectrophotometrical quantitation, 5-10 micrograms of DNA per samples was separated on a 1.5% agarose gel stained with 0.1 microgram/ml ethidium bromide. Fragmented DNA was visualized by exposure to UV light and photographed using a Polaroid MP-4 land camera.

Western Blot Assay

Cells were collected by gentle scraping and centrifuged at 2,500 rpm for 5 minutes at 4° C. The dry pellet was stored at −80° C. until use. Cells were lysed with RIPA buffer (30 mM Tris-Hcl pH=7.4, 0.15 mM NaCl, 1% Nonidet P-40, 0/1% SDS, 0.5% sodium deoxycholate, 1 mM EDTA, 1 mM DTT, 2 mM $MgCl_2$, 0.5 mM PMSF) supplemented with phosphatase and protease inhibitor cocktails (Sigma, St. Louis, Mo.) and sonicated for 1 minute at 25% output power using the Sonicator/Ultrasonic Processor (Misonix, Inc., Farmingdale, N.Y.). Total protein was determined by BCA (Pierce, Rockford, Ill.) and proteins were resolved by SDS-PAGE. Transfer of separated proteins to Schlecher and Schuell nitrocellulose membranes was performed overnight using an electroblotting apparatus. Non-specific binding was blocked by incubating blots for 1 hour at 37° C. in TN-T buffer (0.01 M Tris-Hcl pH=7.4, 0.15 M NaCl, 0.05% Tween 20) containing 1% bovine serum albumin (BSA). After washing with TN-T buffer, the blots were incubated for 2 hours at room temperature with the appropriate antibodies diluted in TN-T buffer containing 0.1% BSA. After three washes with TN-T buffer, the blots were incubated with Protein A-Peroxidase for 1 hour at room temperature. Detection was performed using ECL reagents (Amersham Life Science, Arlington Heights, Ill.) and exposing the blots to high performance chemiluminescence film (Hyperfilm ECL, Amersham Life Science, Arlington Heights, Ill.).

Figure 1B:
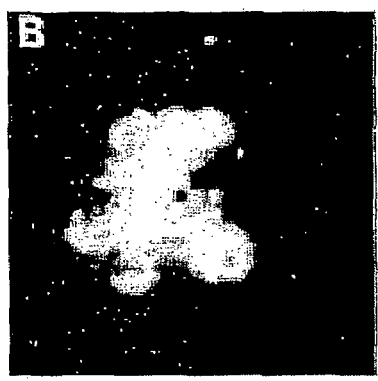
FIG. 1B through 1D are images of photomicrographs depicting the nuclear morphology of TUNEL-stained STS-treated HEK293, JHL15, and JHLA1 cells, respectively.
Figure 1C:
Figure 1D:
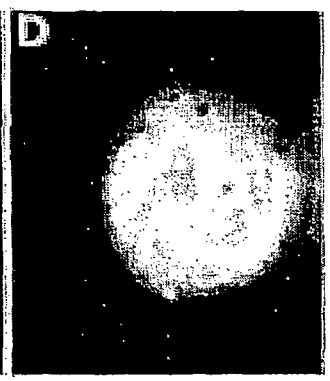

It has been shown previously that the Ras/MEK/MAPK mitogenic pathway is activated in cells that express ICP10PK (JnLa1), but not its PK negative mutant, p138TM (JHL15) (Smith et al., 1994, Virology, 200:598-612). Because this pathway was implicated in the control of apoptosis (Kaplan et al., 2000, Curr. Opin. Neurobiol., 10:381-391), the response of JHLa1, JIL15 and parental (HEK293) cells to the apoptosis inducers STS and D-Mann was examined. HE1K293, JHLA1, and JHL15 cells were treated for 24 hours with 250 nM STS or 300 nM D-Mann and apoptotic cells were quantitated using the TUNEL assay. Results of three independent experiments are expressed as percentage of apoptotic cells±SEM. The proportion of TUNEL-positive cells (apoptotic) was significantly higher is STS-treated HEK293 (71±12.4%) and RHL15 (79±4.9%) than JHLA15 (5.8+2.1%) cells, and similar results were obtained in D-Mann-treated cells (79±7.4%, 58±7%, and 13±8% for HEK293, JHL15, and JHLA15 cells, respectively) (p<0.01 by Student t test) (FIG. 1A). STS-treated, TUNEL-positive HEK293 and JHL15 cells evidenced the hallmark morphological features of apoptosis including cell shrinkage, condensed chromatin, and nuclear fragmentation (FIGS. 1B and 1C), but these features were not observed in the STS-treated, TUNEL negative JHLA1 cells (FIG. 1D). The data indicate that ICP10PK has anti-apoptotic activity, since the only difference between JHLA1 and JHL15 cells is the PK activity of ICP10.

Figure 2:
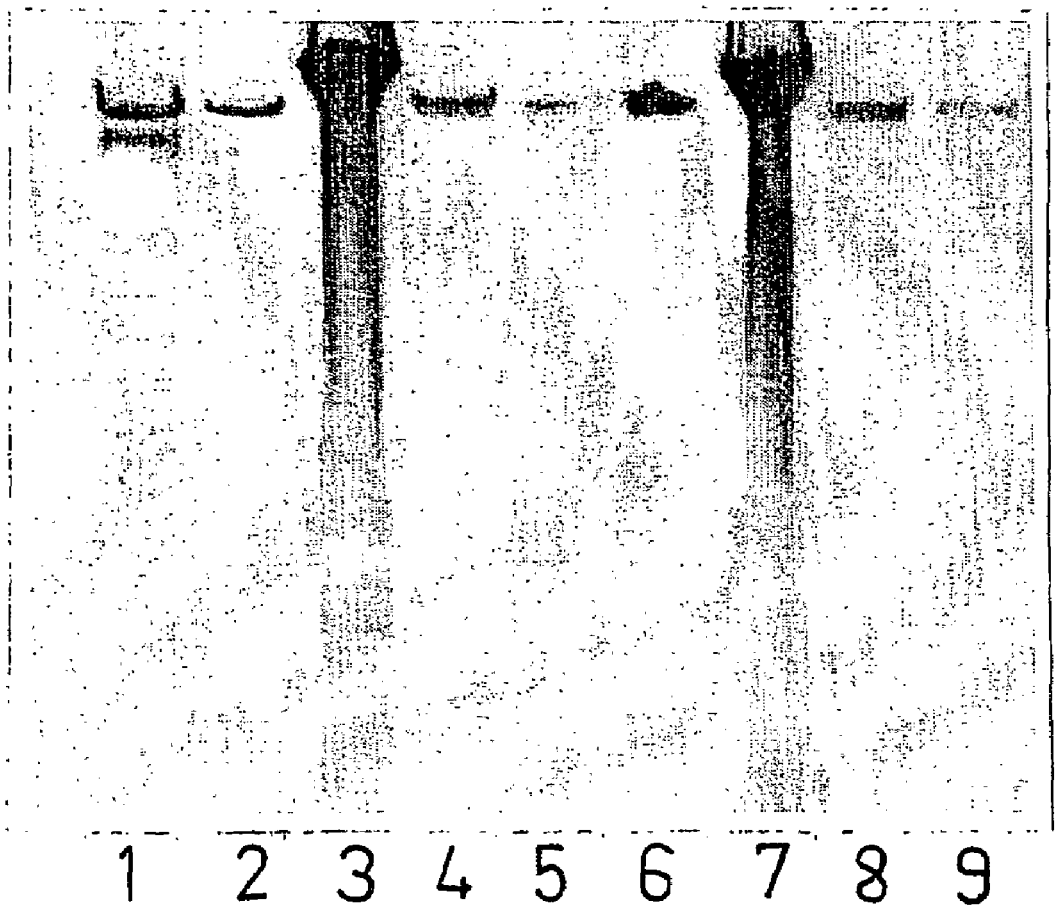
FIG. 2 is an image of an agarose gel depicting inhibition of DNA fragmentation by ICP10PK. BEK293 (lanes 2, 3, 6, and 7) and JHLA1 (lanes 4, 5, 8, and 9) cells were treated with 250 nM STS (lanes 3 and 4) or 300 nM D-Mann (lanes 7 and 8) or mock-treated with DMSO (control for STS; lanes 2 and 5) or MEM (control for D-Mann; lanes 6 and 9).

To determine whether ICP10PK blocks DNA fragmentation induced by STS and D-Mann, treated cells were analyzed using a DNA fragmentation assay which detects degradation of chromosomal DNA into oligonucleosomal fragments. HEK293 cells treated with STS or D-Mann exhibited a DNA ladder pattern characteristic of apoptosis (FIG. 2, lanes 3 and 7, respectively), and similar results were obtained in JHL15 treated cells. In contrast, mock treated HEK293 cells (FIG. 2, lanes 2 and 6) and JHLAI cells treated with STS or D-Mann (FIG. 2, lanes 4 and 8, respectively) did not exhibit DNA fragmentation. These results indicate that ICP10PK blocks fragmentation of cellular DNA induced by apoptotic stimuli.

Figure 3A:
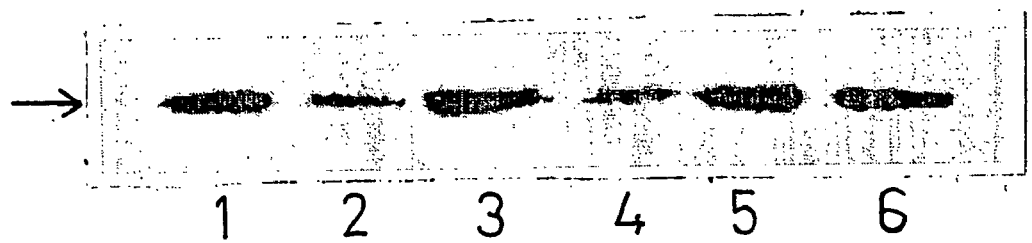
FIG. 3A is an image of an immunoblot depicting inhibition of caspase activation by ICP10PK. Proteins obtained from extracts of HEK293 (lanes 1 and 2), JHL15 (lanes 3 and 4), and JHLA1 (lanes 5 and 6) cells, mock-treated (lanes 1, 3, and 5) or treated (24 hours) with 250 nM of STS (lanes 2, 4, and 6) were resolved by SDS-PAGE (7% acrylamide gels), transferred to nitrocellulose, and immunoblotted with caspase3p32 antibody (specific for the inactive caspase-3 pro-enzyme).
Figure 3C:
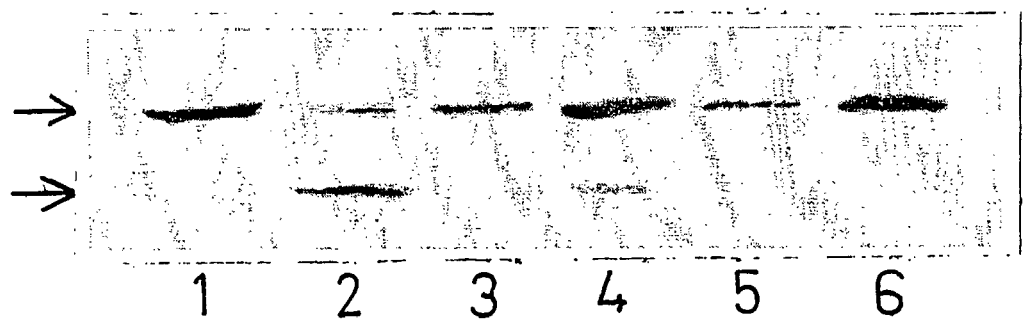
FIG. 3C is an image of an immunoblot depicting inhibition of caspase activation by ICP10PK as evidenced by an assay which measures PARP cleavage. The blot in FIG. 4A was stripped and immunoblotted with anti-PARP antibody. The 85 kDa band consistent with the PARP cleavage product was seen in STS-treated HEK293 (lane 2) and JHL15 (lane 4), but not in JHLA1 (lane 6) cells.
Figure 3B:
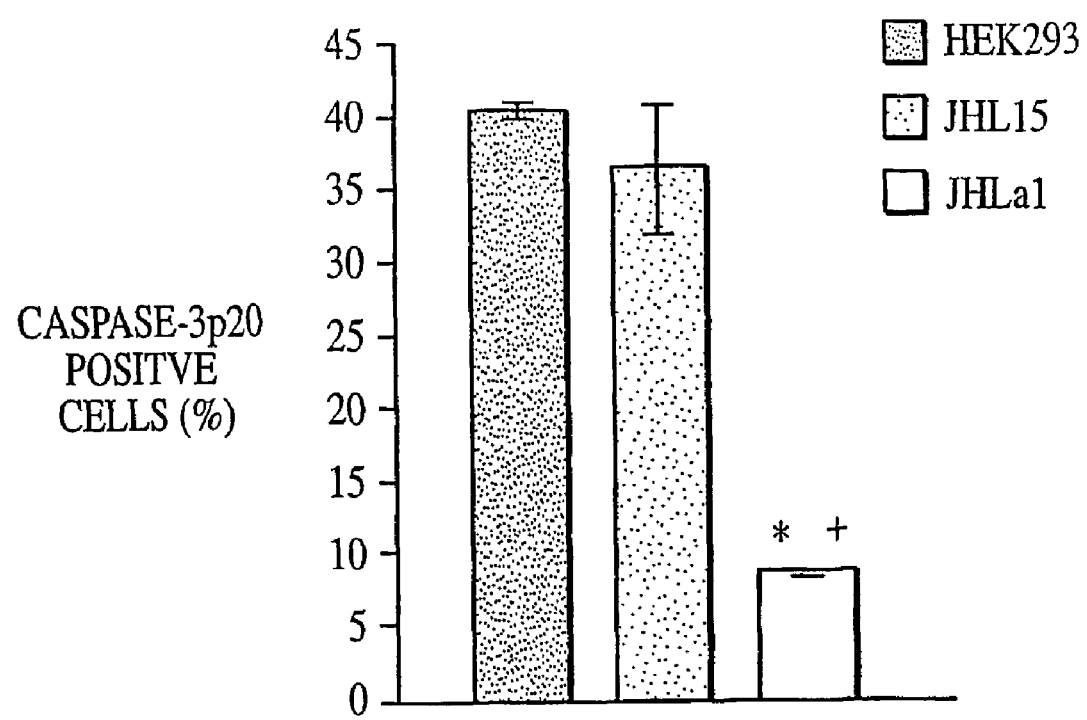
FIG. 3B is a graph depicting inhibition of caspase activation by ICP10PK. HEK93, JHL15, and JHLA1 cells treated with STS (as described in FIG. 3A) were stained with caspase3p20 antibody (specific for the activated caspase-3 which is the large fragment of the pro-enzyme), and cells in five randomly chosen microscopic fields were counted. Results are expressed as mean percentage of positive cells±SEM (*=p<0.01 vs. HEK294; +=p<0.01 vs. JHL15 by Student test).

Previous reports have shown that STS-induced cell death is a caspase-dependent process (Jacobson et al., 1996, J. Cell. Biol., 133:1041-1051). Cleavage of the inactive procaspases (e.g. procaspase-3) causes their activation, and this is a central determinant of many apoptotic processes. To determine whether ICP10PK inhibits cleavage of pro-caspase-3, a central determinant of many apoptotic processes, Western blot analysis was performed on cell lysates obtained from STS-treated cells. A 32 kDa band consistent with the inactive procaspase-3 (caspase-3p32) was detected by immunoblotting with caspase-3p32 antibody in HEK293, JHL15, and JHLA1 cells treated with DMSO (STS diluent) or STS (250 nM). However, densitometric scanning indicated that levels of caspase-3p32 were significantly lower in HEK293 and JBL15 cells treated with STS (FIG. 3A, lanes 2 and 4) than DMSO (FIG. 3A, lanes 1 and 3). The densitometric units were equal to 0.7 for both STS-treated HEK293 and JHL15 cells and 1.0 and 1.1 for DMSO-treated HEK293 and JHL15 cells, respectively). The levels of caspase-3p32 were similar in STS-treated and untreated JHLA1 cells (FIG. 3A, lanes 5 and 6, respectively). In this case, the densitometric units were equal to 1.2 for both treatments. Conversely, the mean percentage of cells positive for the activated caaspase-3 cleavage product (caspase-3p20) was significantly p<0.01 by Student t test) higher in STS-treated HEK293 (40.5±0.9%) and JHL15 (36.4±7.6%) than in STS-treated JHLA1 (9.3±0.1%) cells, as determined by immunohistochemistry with antibody specific for this product (Cell Signaling Technologies, Beverly, Mass.) (FIG. 3B). The data indicate that ICP10PK interferes with caspase-3p32 cleavage/activation.

To determine whether ICP10PK blocks PARP cleavage by caspase-3, a hallmark of caspase-3 dependent apoptosis, Western blot analysis using PARP antibody was performed on STS-treated HEK293, JHL15, and JHLA1 cells. A 116 kDa band consistent with the uncleaved PARP was detected in mock- and STS-treated cells. In contrast, an 85 kDa band consistent with the PARP cleavage product was detected only in STS-treated HEK293 and JHL15 cells (FIG. 3C, lanes 2 and 4, respectively), but not in STS-treated JHLA1 cells (FIG. 3C, lane 6)or mock-treated HEK293, JHL15, JHLA1 cells (FIG. 3C, lanes 1,3, and 5, respectively). These data further suggest that ICP10PK blocks caspase-3 dependent apoptosis.

Taken together, the data presented above demonstrate: (i) ICP10 protects cells against apoptosis induced by STS and D-Mann, suggesting that ICP10 acts on a downstream effector molecule in common to the apoptotic pathway stimulated by these inducers, (ii) ICP10PK inhibits caspase-3 dependent apoptosis, as determined by its ability to inhibit cleavage of procaspase-3 and PARP. However, the ability of ICP10 to inhibit apoptosis is not restricted to caspase-3 and it may involve inhibition of the activation of other caspases as well as the activation of anti-apoptotic proteins involved in the death pathway.

Figure 4A:
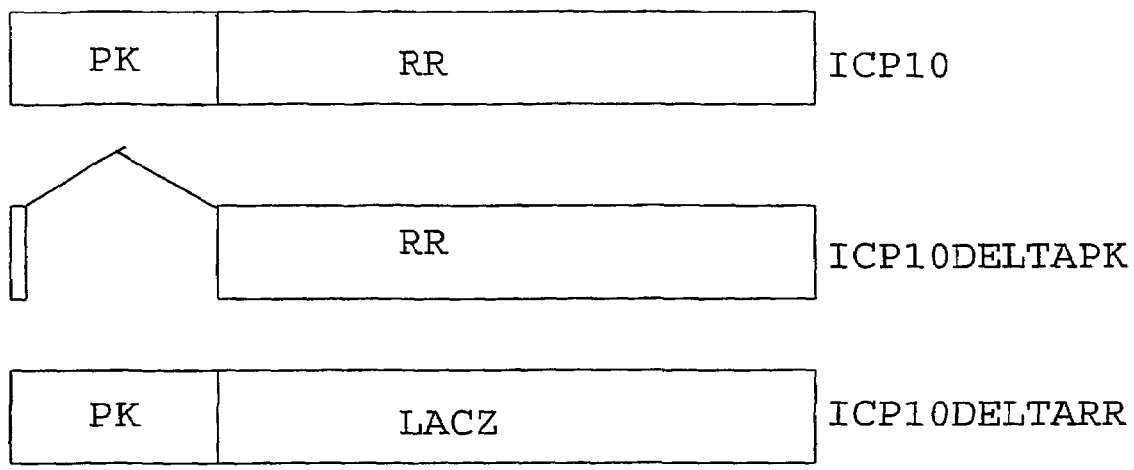
FIG. 4A is a schematic representation of the viral mutants, ICP10deltaPK and ICP10deltaRR.
Figure 4B:
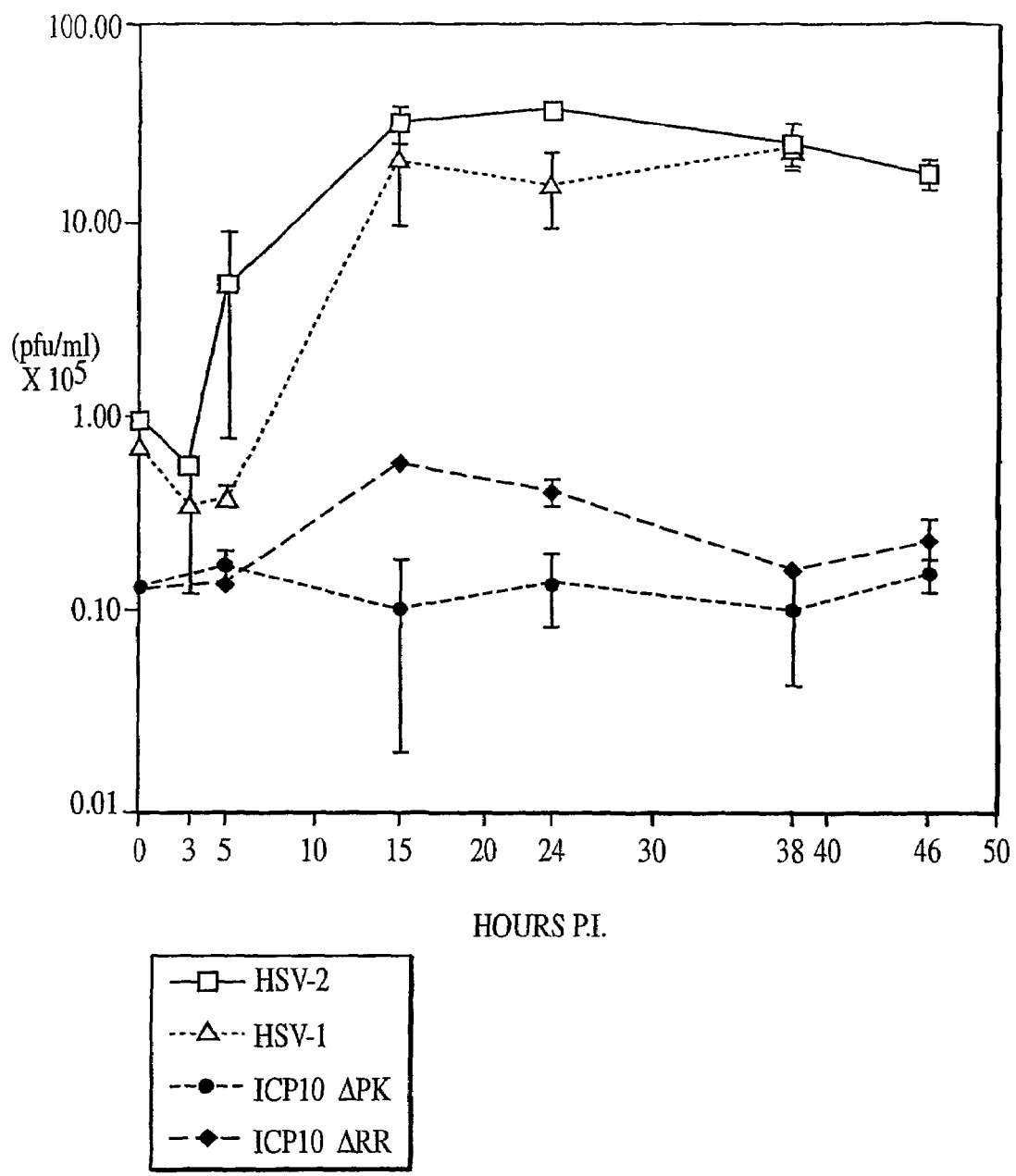
FIG. 4B is a graph depicting virus replication kinetics in hippocampal neurons. Primary cultures of hippocampal neurons were infected with HSV-2, HSV-1, ICP10deltaPK, and ICP10deltaRR at 10 PFU/cell. Viral titers were determined at various times between 0 and 48 hours post infection by plaque assay. Results are expressed as mean PFU/ml±SEM.

To determine whether apoptosis or protection thereof is related to virus replication in hippocampal neurons, primary rat hippocampal cultures (E17-18) were infected with HSV-2, ICP10deltaPK, or ICP10deltaRR (shown schematically in FIG. 4A), and the replication kinetics were evaluated. Briefly, hippocampal neurons at day six in culture were infected with 10 PFU/cell and virus titers were determined by plaque assay at the indicated times post-infection (pi) (FIG. 4B). HSV-2 and HSV-1 replicated equally well in these cells, with growth curves similar to those previously described for other cell types (Smith et al., 1998, J. Virol., 72:9131-9141). Replication began at 3-5 hours p.i. reaching maximal titers at 15-24 hours p.i. ICP10deltaPK and ICP10deltaRR were growth-defective in these cells. These data suggest that ICP10 is required for virus growth.

Figure 5A:
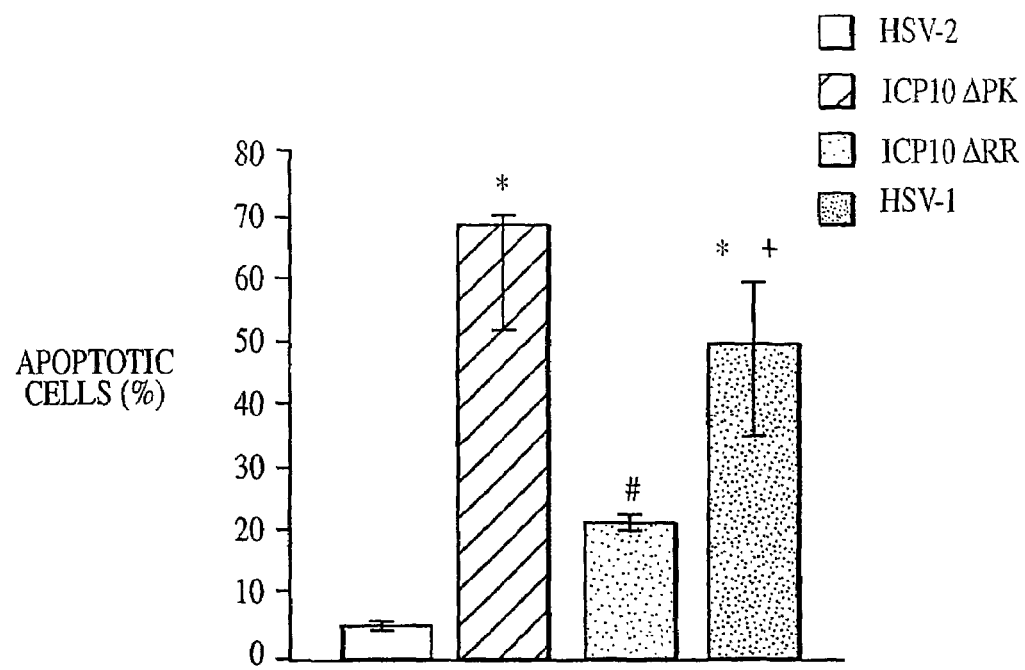
FIG. 5A is a graph depicting anti-apoptotic activity of ICP10PK in virus-infected hippocampal cultures. Primary hippocampal cultures were infected with HSV-2, ICP10deltaPK, ICP10deltaRR, or HSV-1 at 10 PFU/cell and analyzed by TUNEL at 24 hours post infection. Apoptotic (TUNEL-positive) and non-apoptotic (TUNEL-negative) cells were counted in five randomly chosen microscopic fields and the results are expressed as mean percentage of apoptotic cells±SEM. (*=p<0.01 vs. HSV-2; #=p<0.05 vs. HSV-2; +=p>0.05 vs. ICP10deltaPK).
Figure 5E:
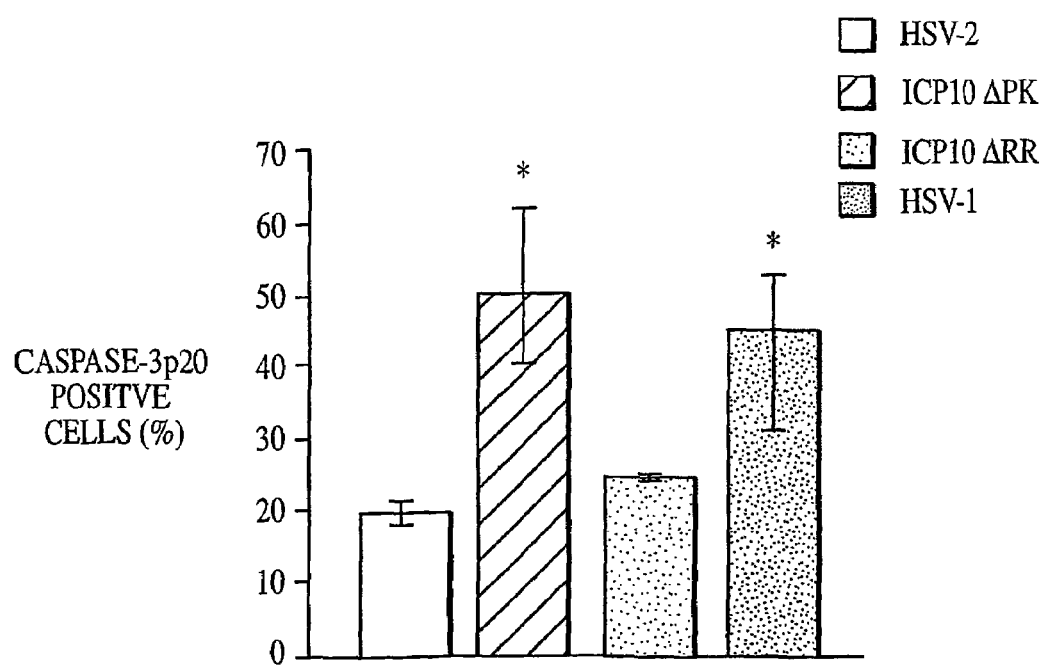
FIG. 5E is a graph depicting inhibition of caspase-3 activation following infection with HSV-2, ICP10deltaPK, ICP10deltaRR, or HSV-1. Cultures in FIG. 5A were stained with caspase-3p20 antibody and counted in five randomly chosen microscopic fields. Results are expressed as mean percentage of positive cells±SEM (*=p<0.05 vs. HSV-2).
Figure 5B:
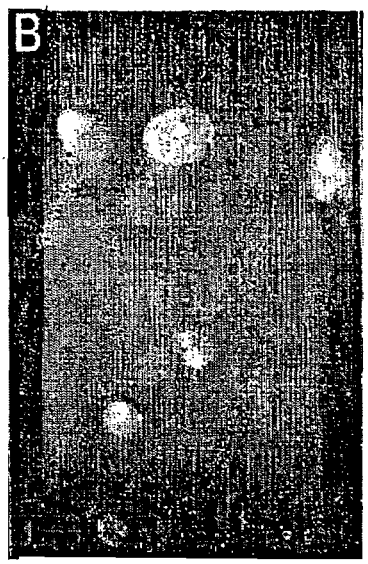
FIGS. 5B through 5D are images of photomicrographs depicting Hoeschst staining of nuclei in cells infected with ICP10deltaPK, HSV-1, and HSV-2, respectively, as described in FIG. 6A.
Figure 5C:
Figure 5D:
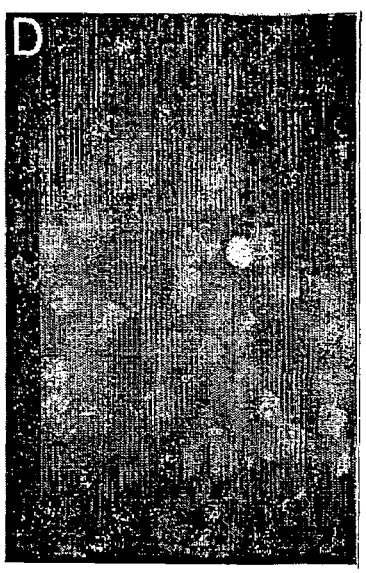

Because anti-apoptotic activity is often cell-type specific, the following series of experiments were designed to test whether ICP10PK has anti-apoptotic activity during viral infection of hippocampal neurons. Cells were infected with 10 PFU/cell of HSV-2 or ICP10deltaPK and apoptosis was determined by TUNEL at 16 and 24 hours p.i. A total of 200-300 cells were counted in five randomly chosen microscopic fields and the mean percentage of TUNEL-positive cells was determined. The data shown in FIG. 5A represent the results of three independent experiments. The percentage of apoptotic cells was significantly lower in cultures infected with HSV-2 than ICP10deltaPK (5.7±0.5% and 68±3.9%, respectively; p<0.01 by Student t test). Apoptosis was also significantly lower in cultures infected with ICP10deltaRR (which retains ICP10PK DNA) than ICP10deltaPK (23±2.1% and 68±3.9% respectively: p°0.01 by Student test). Similar results were obtained at 16 hours p.i. (% apoptotic celss=44±3.5% and 5.4±1.2% for ICP10dletaPK and HSV-2, respectively). The percentage of ICP10deltaPK infected cells that underwent apoptosis increased with increasing multiplicity of infection (2S.6±4.9% and 68±3.9% for 1 and 10 PFU/cell, respectively), but apoptosis was equally low in cultures infected with HSV-2 at both multiplicities if infection (4.8±1.1% and 5.7±0.5% for 1 and 10 PFU/cell, respectively. Staining with the fluorescent DNA-binding dye Hoechst 32258 revealed the presence of nuclear fragmentation characteristic of apoptosis in ICP10deltaPK but not HSV-2-infected cells (FIGS. 5B and 5D, respectively). The data indicate that ICP10PK has anti-apoptotic activity in hippocampal neurons.

Because ICP10PK has limited structure and functional similarity to its HSV-1 counterpart (also known as ICP6PK), we investigated whether ICP6PK also has anti-apoptotic activity in cultures of hippocampal neurons. Cell cultures were infected with HSV-1, HSV-2, ICP10deltaPK, or ICP10deltaRR at 10 PFU/cell and assayed by TUNEL at 24 hours p.i. A similar percentage of TUNEL-positive cells was seen for HSV-1 (50.2±4.5%) and ICP10deltaPK (68±3.9%) (p>0;05 by Student t test) (FIG. 5A). This percentage was significantly higher (p<0.01 by Student t test) than that seen for HSV-2 (5.7±0.5%) or ICP10deltaRR (23+2.1%) HSV-1-infected hippocampal neurons also evidenced nuclear fragmentation patters characteristic of apoptosis (FIG. 5C).

Since TUNEL may be an unreliable assay due to label incorporation at sites of random DNA degradation and the results obtained with constitutively expressing cells indicated that ICP 10PK blocks caspase-3 dependent apoptosis, caspase-3 activation in hippocampal cultures was analyzed. Cultures were infected for 24 hours with HSV-2, ICP10deltaPK, ICP10deltaRR, or HSV-1 at 10 PFU/cell and stained with caspase-3p20 antibody. The percentage of caspase-3p20-positive cells was significantly higher in cultures infected with ICP10deltaPK (52.6±9.6%) or HSV-1 (47.4±%) than HSV-2 (19.3±2%) or ICP10deltaRR (26±0.2%) which retains ICP10PK DNA (p<0.05 by Student t test) (FIG. 5E). The data are comparable to those obtained by TUNEL, supporting the conclusion that ICP10PK, but not its HSV-1 counterpart (ICP6PK), has anti-apoptotic activity in primary cultures of hippocampal cells.

Figures 6A, 6B, 6C:
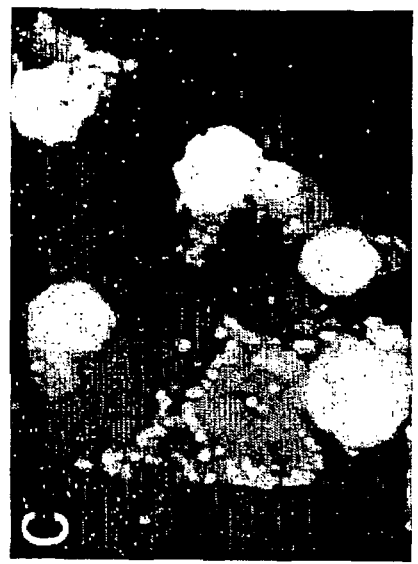
FIGS. 6A trough 6F are a series of images of photomicrographs depicting neuron-specific antibody staining of TUNEL-positive, virus-infected cells. Primary hippocampal cultures were infected for 24 hours at 10 PFU/cell with ICP10 deltaPK FIGS. 6A through 6C) or HSV-1 (FIGS. 6D through 6F). TUNEL-positive cells (FITC labeled.
Figures 6D, 6E, 6F:

The primary hippocampal cultures used in these studies are likely to consist of various cell subpopulations. Therefore, to identify the cells type(s) that become apoptotic upon infection with ICP10deltaPK or HSV-1, cell cultures were infected for 24 hours with ICP10deltaPK or HSV-1 at 10 PFU/cells. Cells were double stained with fluorescein (FITC)-labeled dUTP (TLINEL) and phycoerythrine (PE)-labeled antibodies specific for different cell subpopulations. TUNEL-positive cells were observed in cultures infected with ICP10deltaPK (FIG. 6A) or HSV-1 (FIG. 7D) and also stained with TUJ-1 antibody (FIGS. 6B and 6E) which is specific for postmitotic neurons (Fereira et al., 1992, J. Neurosci. Res., 32:516-529). The TUJ-1 staining (PE) localized in the cell bodies and neurites while the FITC staining (TUNEL) was nuclear (FIGS. 6C and 6F). TUNEL-positive cells did not stain with glial fibrillary acidic protein (GFAP) or galactocerebroside (GalC) antibodies that are specific for astrocytes and oligodendrocytes, respectively. The data indicate that the apoptotic cells are neurons. By inference, ICP10PK, but not ICP6PK, protects hippocampal neurons against apoptotic stimulus.

Figure 7A:
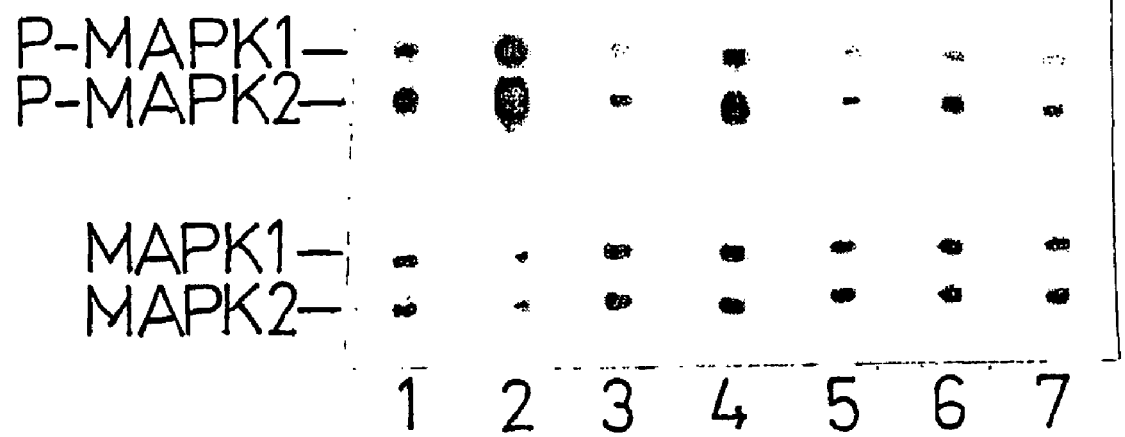
FIG. 7A is an image of an immunoblot depicting activation of the MEK/MAPK pathway by HSV-2. Primary cultures of hippocampal neurons were infected at 10PFU/cell with HSV-2, ICP10deltaPK, or HSV-1 or mock-infected with growth medium and harvested and 0.5 and 24 hours p.i. Proteins were resolved by SDS-PAGE (8.5% acrylamide gels), transferred to nitrocellulose membranes, and immunoblotted with antibody specific for P-MAPK1/2. Blots were stripped and re-blotted with antibody to MAPK1/2, and protein levels were quantitated by densitometric scanning.
Figure 7C:
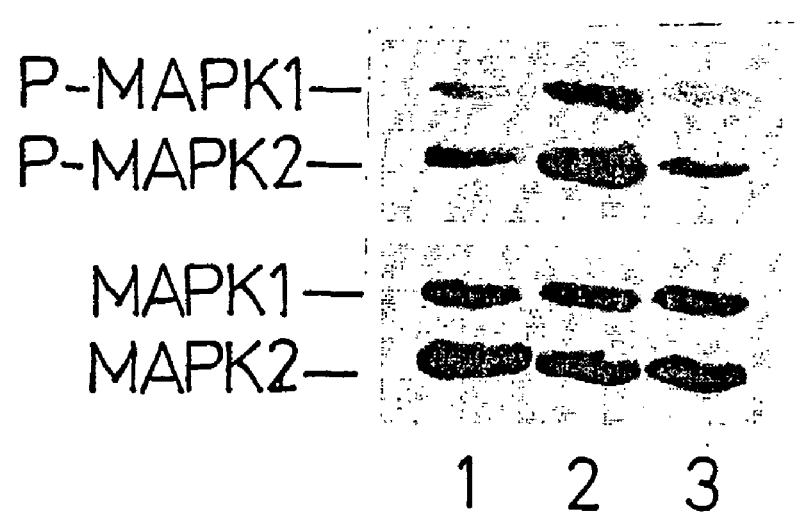
FIG. 7C is an image of an immunoblot depicting the ability of the MEK-specific inhibitor, U0126, to inhibit activation of P-MAPK1/2 by HSV-2. Extracts obtained from cells mock-infected (lane 1) or infected with HSV-2 in the absence (lane 2) or presence (lane 3) of 20 micromoles of U0126, were immunoblotted with antibody specific for P-MAPK1/2 (upper bands) or MAPK1/2 (bottom bands).
Figure 7B:
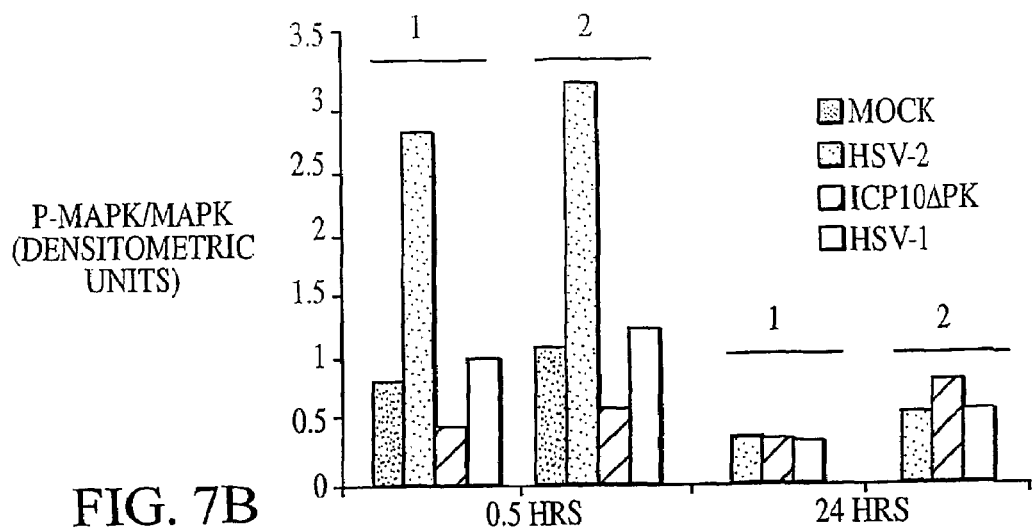
FIG. 7B is a graph depicting the results of densitometric scanning of bands in FIG. 8A. Results are expressed as ratios of P-MAPK1/MAPK1 (MAPK1) and P-MAPK2/MAPK2 (MAPK2).
Figure 8A:
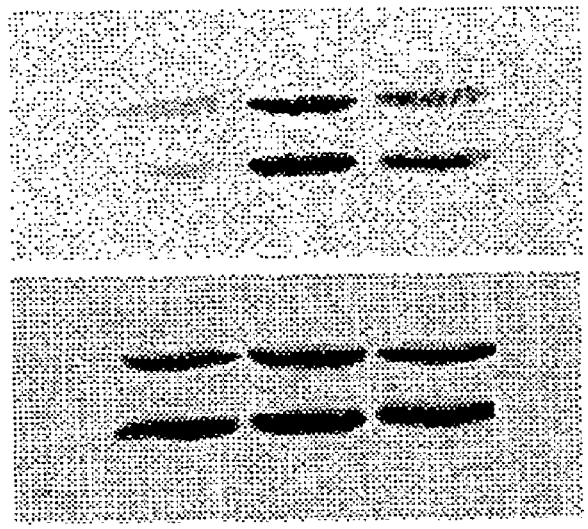
FIG. 8A is an image of an immunoblot depicting the inability of antibody neutralized HSV-2 to activate MAPK. Extracts obtained from cells mock-infected (lane 1) or infected with HSV-2 (lane 2) or HSV-2 neutralized with the IgG fraction from a gD monoclonal antibody (lane 3) were immunoblotted with antibody specific for P-MAPK1/2 (upper bands) or MAPK1/2 (bottom bands).

Having shown that ICP10PK has anti-apoptotic activity in hippocampal neurons, it was of interest to determine whether this activity is related to its ability to activate the MEK/MAPK pathway (Smith et al., 1994, Virology, 200:598-612; Smith et al., 2000, J. Virol., 74:10417-10429). Culture of hippocampal neurons were infected with HSV-2 or ICP10deltaPK at 10 PFU/cell and analyzed for MAPK activation by immunoblotting with antibodies specific for the unphosphorylated (MAPK) and phosphorylated (activated) MAPK species (P-MAPK1/2). HSV-1 was used as a control because (i) it does not activate MEK/MAPK (McLean et al., 1999, J. Virol., 73:8415-8426; Zachos et al., 1999, J. Biol. Chem., 274:5097-5103) and (ii) ICP6PK does not have anti-apoptotic activity. Cell extracts were studies at 0.5 and 24 hours p.i. (0 hours p.i. is at the end of adsorption). At 0.5 hours p.i., P-MAPK1/2 levels were significantly higher in HSV-2-infected (FIG. 7A, lane 2) than mock-infected (FIG. 7A, lane 1) cells. The increased levels of P-MAPK1/2 in HSV-2 infected cells reflect MAPK activation by ICP10PK because (i) P-MAPK1/2 levels were not increased in cells infected with ICP10deltaPK (FIG. 7A, lane 2) or HSV-1 (FIG. 7A, lane 4) and (ii) the levels of the unphosphorylated MAPK species were similar in all cultures (FIG. 7A, bottom). MAPK activation was not observed at 24 hours p.i., and similar P-MAPK1/2 levels were observed in all cultures (FIG. 7A. lanes 5-7). Densitometric scanning of the bands in FIG. 8A support these conclusions (FIG. 7B).

Figure 7D:
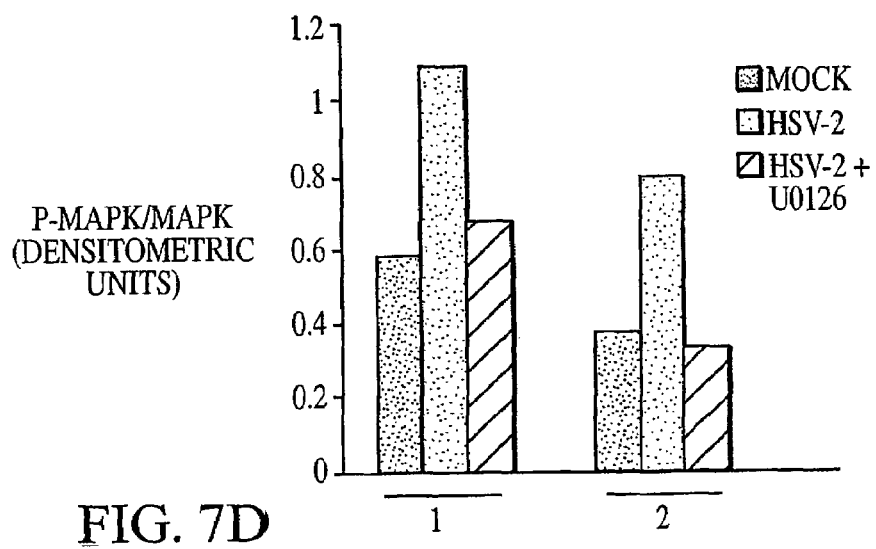
FIG. 7D is a graph depicting the results of densitometric scanning of bands in FIG. 8C. Results are expressed as ratios of P-MAPK1/MAPK1 (MAPK1) and P-MAPK2/MAPK2 (MAPK2).
Figure 7E:
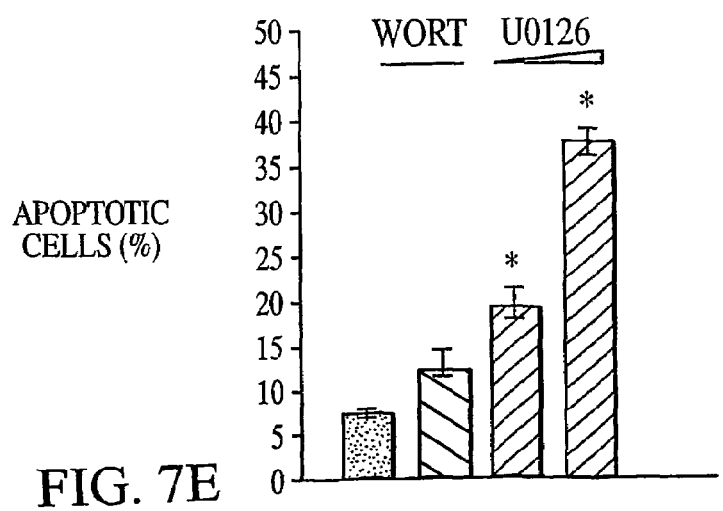
FIGS. 7E and 7F are graphs depicting the effect of LY294002 and U0126 inhibitors (which are respectively specific for P13-K/Akt and MEK) on HSV-2-induced apoptosis. Hippocampal cultures were either mock infected or infected with HSV-2 (10 PFU/cell; 24 hrs) in the absence or presence of 0-100 micromolar LY294002 or 0-20 micromolar U0126, and analyzed by TUNEL. Cells were counted in five randomly chosen microscopic fields and the results are expressed as mean percentage TUNEL-positive cells±SEM (*=p<0.01 vs. untreated HSV-2 infected cells).

To examine the contribution of upstream components of the Ras survival pathway towards MIAPK activation, hippocampal cultures were infected with 5 HSV-2 in the presence (or absence) of 20 micromoles of the MEK-specific inhibitor U0126 and cell extracts were examined for P-MAPK1/2 by immunoblotting with specific antibody. P-MAPK1/2 levels were significantly lower in cells treated with U0126 (FIG. 7C, lanes 2 and 3; FIG. 7D) than in untreated cells (FIG. 7C, lane 2; FIG. 7D), suggesting that MPAK activation is MEK dependent. Presumably MEK/MAPK activation is responsible for the anti-apoptotic activity of HSV-2, since U0126 treatment of HSV-2 infected cultures caused a dose-dependent increased in the percentage of TUNEL-positive (apoptotic) cells (20±1.6% and 39.3±2.8% for 10 and 20 micromoles, respectively, as compared to 7.2±0.7% in untreated cells; p<0.01 by Student t test) (FIG. 7E).

Figure 7F:
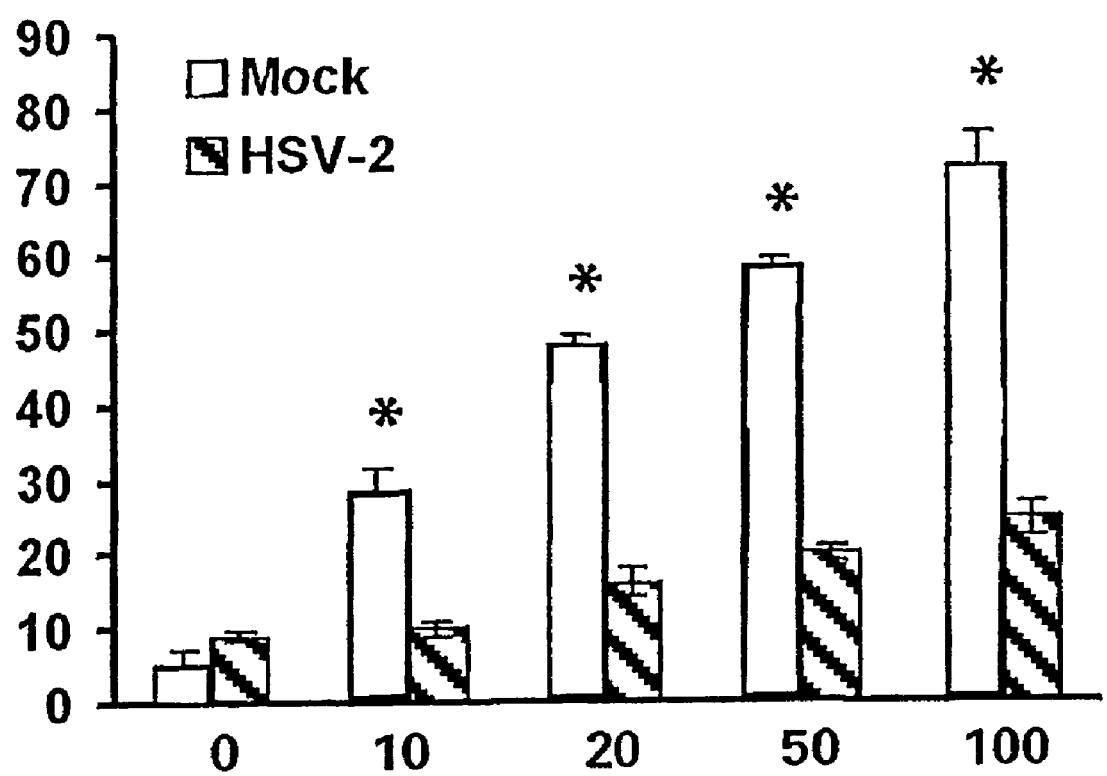

The possibility that P13-kinase activation is also involved in the anti-apoptotic activity of HSV-2 was considered, because the P13-kinase/Akt pathway functions in growth factor initiated survival in neurons (Kaplan et al., 2000, Curr. Opin. Neurobiol., 10:381-391). However, the percentage of TUNEL-positive cells in hippocampal cultures infected with HSV-2 in the presence of LY294002 [at concentrations (10-100 micromolar) at which it specifically inhibits P13-kinase] (Crowder et al., 1998, J. Neurosci., 18:2933-2943) were only minimally increased [from 9.1±1 (untreated) to 24.8±2.3 (when treated with 100 micromolar LY294002)] and died more slowly (p<0.01 by ANOVA) than the mock-infected cells treated with inhibitor [5±3 (non-treated) to 72±4.5 (when treated with 100 micromolar LY294002)] (FIG. 7F). Same kinetics were observed when cells were treated with wortmannin (Yano et al., 1998, Nature, 396:584-587) at concentrations (100-200 nanomolar) that specifically inhibit PI3-K (data not shown). These data suggest that PI3-K has only minimal contribution to the survival of HSV-2 infected hippocampal neurons, but it is however required for the basal maintenance of these cells, at least under the present experimental conditions.

Figure 8C:
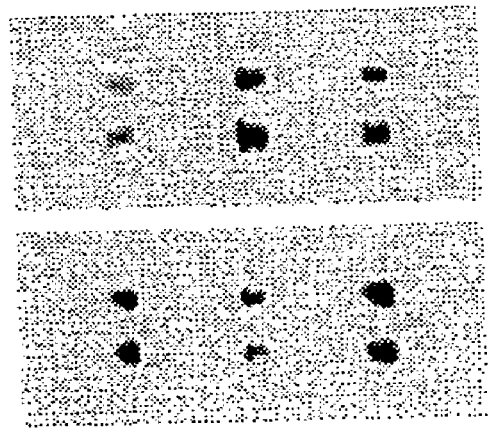
FIG. 8C is an image of an immunoblot the inability of HSV-2 neutralized with anti-HSV-2 (hyperimmune) serum to activate MAPK. Extracts obtained from cells mock-infected (lane 1) or infected with HSV-2 neutralized with preimmune (lane 2) or HSV-2 hyperimmune (lane 3) serum were immunoblotted with antibody specific for P-MAPK1/2 (upper bands) or MAPK (bottom bands).
Figure 8B:
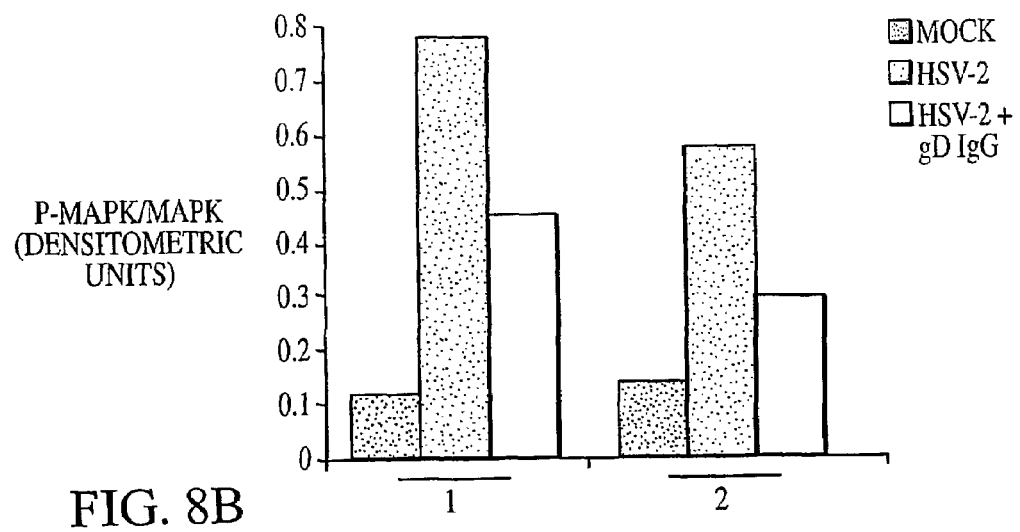
FIG. 8B is a graph depicting the results of densitometric scanning of the bands in FIG. 8A. Results are expressed as ratios of P-MAPK1/MAPK1 (MAPK1) and P-MAPK2/MAPK2 (MAPK2).
Figure 8D:
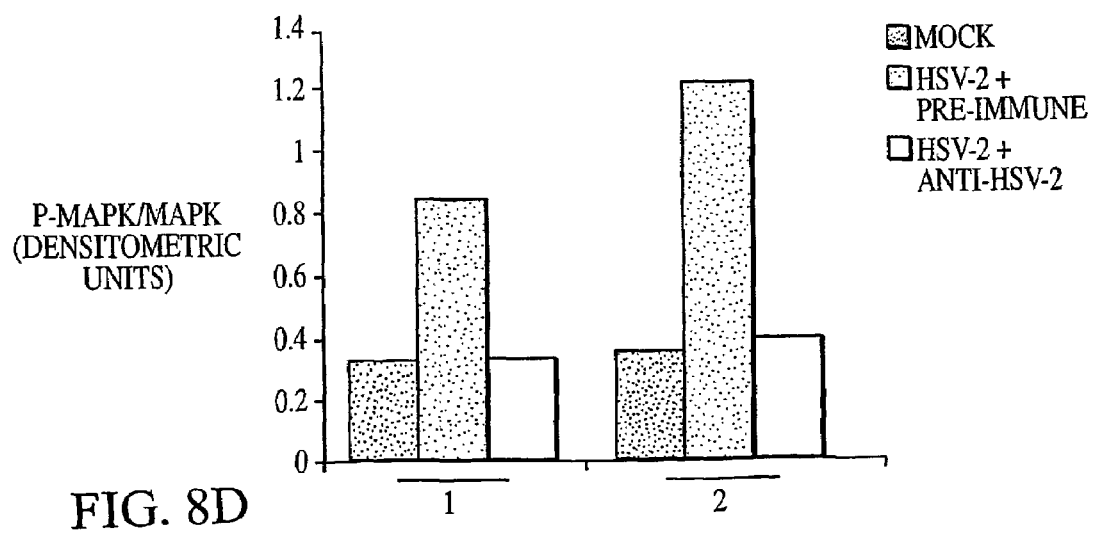
FIG. 8D is a graph depicting the results of densitometric scanning of the bands in FIG. 8C. Results are expressed as ratios of P-MAPK1/MAPK1 (MAPK1) and P-MAPK2/MAPK2 (MAPK2).

The finding that MEK/MAPK are activated in hippocampal cells at 30 minutes, but not 24 hours p.i. is amenable to two potential interpretations. According to the first interpretation, MEK/MAPK activation (and, therefore, anti-apoptotic activity is mediated by the ICP10 PK located in the tegument of the incoming virion (Smith et al., 1997, Virology, 234:235-242). Implicit in this interpretation is the assumption that cellular penetration and virion uncoating are required for both processes. An alternative interpretation is that MEK/MAPK are activated by virus binding to receptors on the cell surface, and both it and the resulting anti-apoptotic effect are independent of cell penetration. This possibility is particularly significant because the HSV receptor can generate a signal that regulates AP-1 upon ligand binding (Marsters et al., 1997, J. Biol. Chef., 272:14029-12032). To determine whether MEK/MAPK activation is dependent on cellular penetration, cultures of hippocampal neurons were infected with antibody-neutralized HSV-2 that binds, but does not penetrate the cells (Highlander et al., 1987, J. Virol., 61:3356-3364). Cells were examined for MAPK activation by immunoblotting with antibody specific for P-MAPK1/2 at 30 minutes p.i. P-MARK1/2 levels were significantly lower in cells exposed to virus neutralized with a monoclonal antibody to glycoprotein D (gD Mab) (FIG. 8A, lane 3; FIG. 8B) or HSV-2 antiserum (FIG. 8C, lane 3; FIG. 8D) than non-neutralized virus (FIG. 8A, lane 2; FIG. 8B) or virus neutralized with pre-immune serum (FIG. 8C, lane 2; FIG. 8D). The superior effect of the anti-HSV-2 serum relative to the gD Mab presumably reflects the broader antigenic specificity of the antiserum. These data suggest that cell penetration is required for MEK/MAPK activation.

Figure 9:
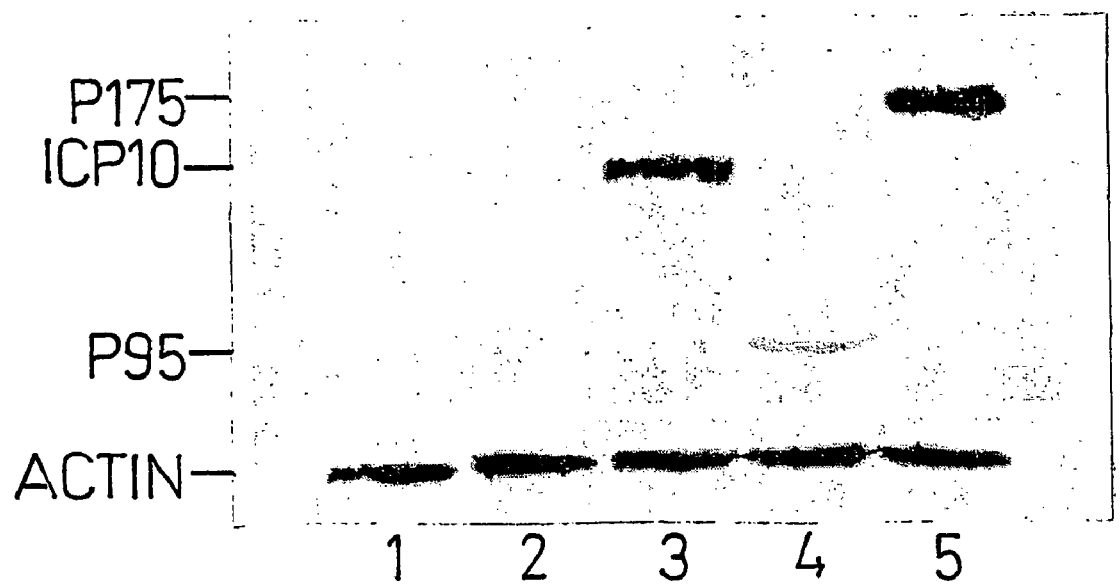
FIG. 9 is an image of an immunoblot depicting expression of ICP10 and mutant forms of ICP10 in primary cultures of hippocampal neurons. Extracts from cells mock-infected (lane 1) or infected (10 PFU/cell; 0.5 hours) with HSV-2 neutralized with gD monoclonal antibody (lane 2), HSV-2 (lane 3), ICP10deltaPK (lane 4), or ICP10deltaRR (lane 5) were immunoblotted with ICP10 antibody. Blots were stripped and reprobed with actin antibody as a control for loading and protein expression.

Implicit in the assumption that cell penetration is required for MEK/MAPK activation and anti-apoptotic activity is the conclusion that both are mediated by the ICP10 PK located within the virion tegument, which is released upon virion uncoating (Smith et al., 1997, Virology, 234:235-242). To test this hypothesis, extracts of cells infected with HSV-2, ICP10deltaPK, ICP10deltaRR or neutralized HSV-2 were obtained at 30 minutes p.i. and immunoblotted with antibody that recognizes ICP10 and its mutants (p95 and p175 for ICP10deltaPK and ICP10deltaRR, respectively). ICP10 (FIG. 9, lane 3), p95 (FIG. 9, lane 4) and p175 (FIG. 9, lane 5) were observed in extracts of cells infected with HSV-2, ICP10deltaPK and ICP10deltaRR. However, these proteins were not observed in extracts from cells infected with neutralized HSV-2 (FIG. 9, lane 2), consistent with the failure of the neutralized virus to penetrate the cells (Highlander et al., 1987, J. Virol., 61:3356-3364). The data indicate that MEK/MAPK activation and anti-apoptotic activity are mediated by the virion ICP10 PK and require cell penetration/virion uncoating.

Example 2

The Use of HSV-2 ICP10PK to Treat Neurodegenerative Disorders

The data herein demonstrate the ability of ICP10PK to protect cells from apoptotic stimuli specific for neurodegenerative disorders such as growth factor deprivation and genetic defects. Also demonstrated herein is delivery of ICP10PK to the CNS upon non-invasive, peripheral administration, using a viral vector.

The materials and methods used in the experiments presented in this example are now described.

Transfection of PC12 Cells

PC12 cells were cultured in DMEM/F12 (Gibco-BRL) with 10% fetal bovine serum (FBS) (Gemini), 0.36% D-glucose (Sigmna), 0.21% sodium bicarbonate, 0.009% gentamycin and 100 ng/ml NGF (Roche Molecular Biochemicals) and transfected [using FuGene 6 Transfection Reagent (Roche Molecular Biochemicals)] with vectors pJW17 or pJHL15 that respectively express ICP10 or a TM deleted PK negative ICP10 mutant (p139™) (Luo et al., 1992, J. Biol. Chem., 267:9645-53; Smith et al., 1994, Virology, 200:598-612). At 24 hours post-transfection, the cells were washed and the medium was replaced with medium free of NGF.

Cell Viability Assay

Cell viability was determined using CellTiter 96 Aqueous One Solution Cell Proliferation Assay (Promega) that measures enzymatic activity of functional mitochondria, according to the manufacturer instructions.

The next series of experiments were designed to test the therapeutic value of ICP10PK in treating neurodegenerative disorders. Thus, the effect of ICP10 PK on: i) neuronal apoptosis induced by apoptosis stimulus specific for these neurological conditions (loss of trophic support), and ii) accelerated neuronal death of trisomy 16 (a naturally occurring mouse genetic disorder) hippocampal neurons was tested.

Because Ras/MEK/MAPK is involved in neurotrophin-mediated neuronal survival, it was of interest to determine whether ICP10 PK may also promote survival in experimental paradigms created by trophic factor deprivation or genetic defects in neurotrophin receptor signaling. In a first series of experiments rat pheochromocytoma (PC12) cells were used as an in vitro model to test this hypothesis. When growth in NGF containing medium, PC12 cells acquire properties of sympathetic neurons (neurite outgrowth, electrical excitability and expression of specific neuronal markers) and die by apoptosis upon NGF withdrawal (Greene et al., 1982, Adv. Cell. Neurobiol., 3:373-414). Because these cells can be rescued by the addition of NGF (Greene et al., 1982, Adv. Cell. Neurobiol., 3:373-414), the ability of 1CP10PK to substitute for NGF with respect to its ability to support survival of differentiated PC12 cells was evaluated. PC12 cells were transfected with vectors encoding ICP10 and p139™, and ICP10 and p139™ expression was examined at 24 hours post-transfection by straining with an ICP10-specific antibody (recognizes amino acids 13-26 in both proteins), as previously described (Aurelian et al., 1989, Cancer Cells, 7:187-191).

Figure 10:
FIGS. 10A through 10C are a series of images of photomicrographs depicting expression of ICP10PK and p139™ in transfected PC12 cells. Differentiated PC12 cells non-transfected, transfected with pJW17 or pJHL15 (FIGS. 10A, 10B, and 10C, respectively) were fixed with 3% paraformaldehyde at 24 hours post-transfection and stained with ICP10-specific antibody by immunohistochemistry. Staining is cytoplasmic (arrowhead). Nuclei are counterstained with hematoxylin (arrow).

Expression of the transfected genes was detected in approximately 35-50% of the cells. Staining was localized in the cytoplasm and both its intensity and the proportion of stained cells were similar for pJW17 (FIG. 10B) and pJHL15 (FIG. 10C), suggesting that ICP10 and p139™ are expressed equally well. Staining was specific, and was not seen in control (non-transfected) PC 12 cells (FIG. 10A). Morphologically, the non-transfected PC12 cells (FIG. 10A) exhibited degenerated cell bodies and "beading" of neurites starting at approximately 24 hours after NGF removal, while the pJW17-transfected cultures were debris-free, with long neurites and cell bodies resembling those of NGF-treated PC12 cells.

Figure 11:
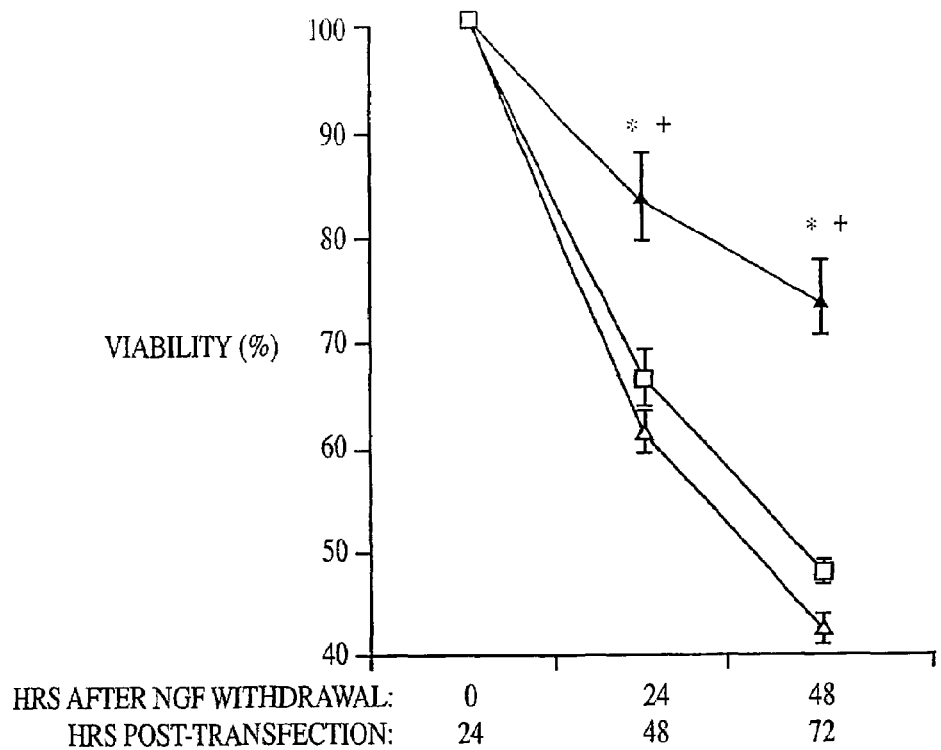
FIG. 11 is a graph depicting the ability of ICP10PK to protect PC12 cells from death induced by NGF withdrawal. PC12 cells were differentiated by growth (at least twelve days) in serum-free medium supplemented with 100ng/ml of NGF. Cells were transfected with expression vector pJW17 (ICP10PK; solid triangles) or pJHL15 (p139TM: open triangles) or not transfected (open squares). Cell viability is expressed as percentage relative to the number of cells at 0 hours post NGF withdrawal±SEM (*=$p<0.05$ vs. control +=$p<0.05$ vs.pJHL15-transfected cells, by ANOVA with Tukey-Kramer post-test).

Cell viability was determined at 24, 48 and 72 hours post-transfection (0, 24 and 48 hours post-NGF withdrawal). Results are expressed as % viable cells ±SEM relative to 0 hours after NGF withdrawal. The kinetics of cell death in the non-transfected and pJHL15-transfected cells were similar to those previously reported for this system (Pittman et al. 1993), with a respective survival of 65.7±2.7% and 61.2±1% at 24 hours after NGF withdrawal and 48.1±1% and 43.1±1.4% at 48 hours after NGF withdrawal (FIG. 11). By contrast, survival of pJHL17-transfected cells was 82.3±3.9% and 73.2±3.3% at 24 and 48 hours after NGF removal ($p<0.05$ vs. control and pJHL15 transfected cells, by ANOVA), suggesting that ICP10 PK can compensate for the absence of NGF.

Figure 12:
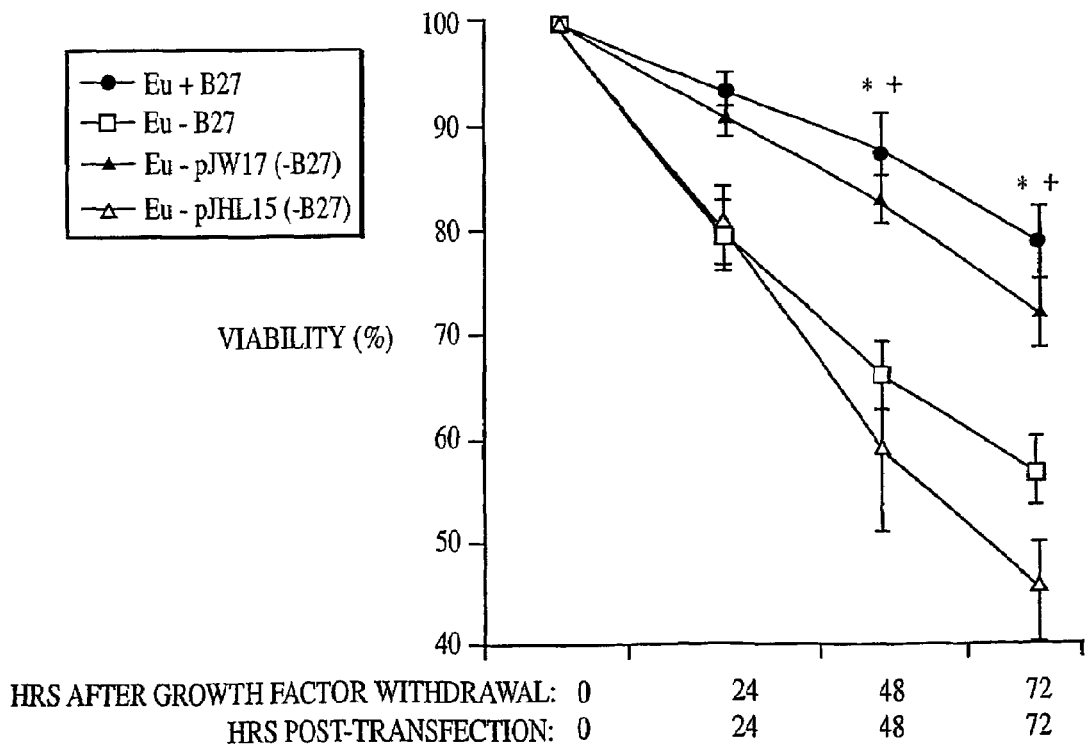
FIG. 12 is a graph depicting the ability of ICP10PK to rescue hippocampal neurons from death due to growth factor deprivation. Mouse hippocampal neurons were plated on glass coverslips, maintained for two days in MEM with B27 supplement (Gibco BRL, Gaithersburg, Md.) which contains optimized concentrations of neuron growth factors, transfected with pJW17 (solid triangles) or pJHL15 (open triangles), and the medium was replaced with MEM free of serum or B27. Non-transfected cells were maintained in MEM (Eu-B27; open squares) or MEM with B27 (Eu+B27; solid circles). Viability was determined by counting live neurons and expressed as a percentage relative to the initial (t=0) number of viable cells±SEM (*=$p<0.05$ vs. control, Eu-B27; +=$p<0.05$ vs. pJHL15-transfected cells, but ANOVA with Tukey-Kramer post-test).

To further examine the role of ICP10PK in neuronal survival, the experiment was repeated with primary hippocampal culture from embryonic day 16 (E16) mice, established and grown as previously described (Bambrick and Krueger, 1999) on glass coverslips etched with a grid of 175×175 micrometer squares (CELLocate; Eppendorf) in MEM with B27 supplement (Gibco) which contain optimized concentrations of neuron survival factors. At 2 days in culture, the cells were transfected with pJW17 or pJHL15 and the medium was replaced with NEM free of serum and growth factors (0 hours) as described above. Control non-transfected cultures were maintained in medium with (Eu+B27) or without (Eu-B 27) the B27 supplement and neuronal survival was determined by counting live cells (phase-dark bodies and fine neurites) in seven randomly chosen squares (Bambrick et al., 1999, J. Neurochem., 72:1769-1772). Neuronal identity was confirmed by staining with the neuron-specific antibody to beta tubulin (TuJ1) (Ferreira et al., 1992, J. Neurosci. Res., 32:516-529). The results are expressed as percentage of surviving cells±SEM relative to 0 hours. The % surviving cells were respectively 52.6±7.2% and 56±3.1% for Eu-B27 and pJHL 15-transfected cells at 48 hours and 34.3±7.6% and 34.8±3.8% at 72 hours after B27 withdrawal. The viability of pJW17-transfected cells was significantly (p<0.05 by ANOVA) higher (80.6±2.7% and 67.7±2.4% at 48 and 72 hours, respectively) and similar to that of Eu+B27 cells (88.7+3.1% and 80.6+2.7% at 48 and 72 hours, respectively) (FIG. 12). These data are consistent with those obtained for differentiated PC12 cells and indicate that ICP10PK also promotes the survival of hippocampal neurons in the absence of growth factors.

Figure 13:
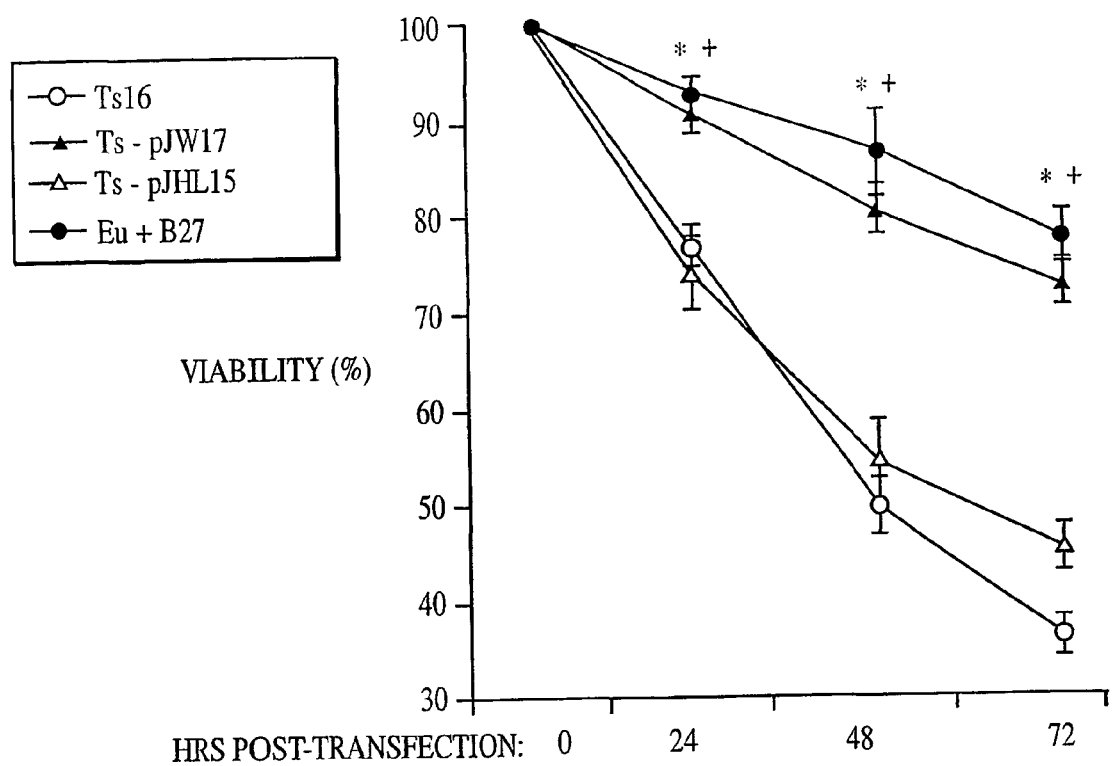
FIG. 13 is a graph depicting the ability of ICP10PK to block the death of Ts16 hippocampal neurons. Ts16 mouse hippocampal neurons were grown as described in FIG. 12, and transfected with pJW17 (solid triangles), pJHL15 (open triangles), or non-transfected (open circles). Non-transfected euploid hippocampal cells maintained in B27-supplemented medium (Eu+B27; solid circles) were used as a control. Viability was determined by counting live neurons and expressed as a percentage relative to the initial (t=0) number of viable cells±SEM (*=$p<0.001$ vs. control Ts16 non-transfected; +=$p<0.001$ vs. pJHL15-transfected cells, by ANOVA with Tukey-Kramer post-test).
Figure 15:
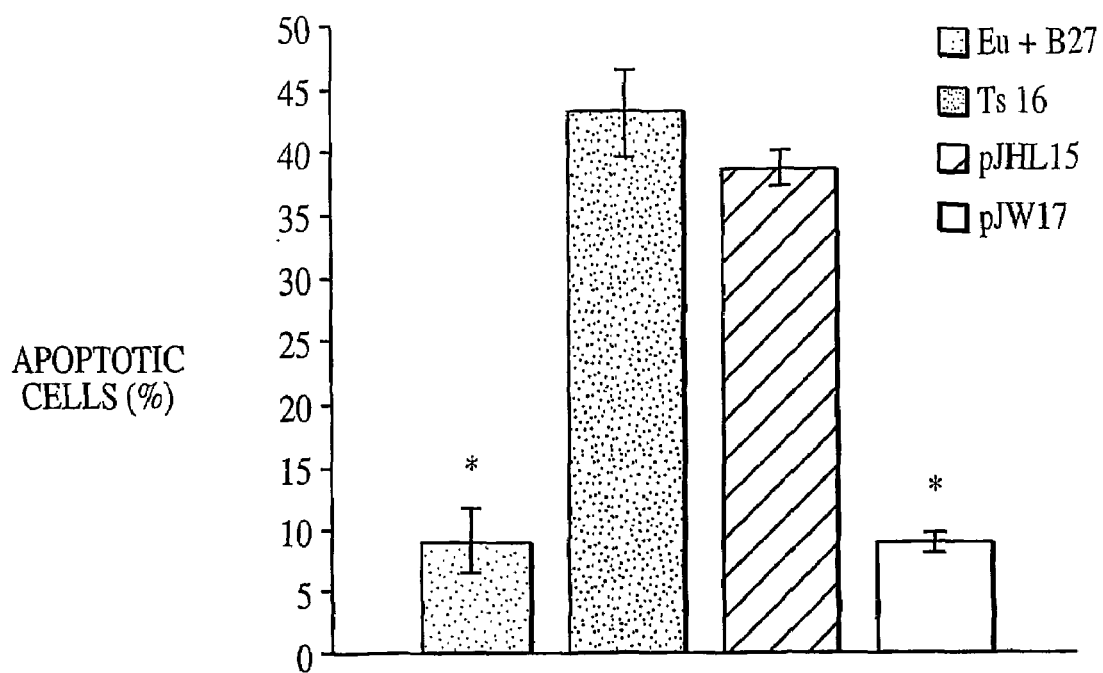
FIG. 15 is a graph depicting the ability of ICP10PK to inhibit apoptosis in Ts16 hippocampal neurons. Ts16 mouse hippocampal neurons were grown and transfected with pJW17, pJHL15, or remained non-transfected. Non-transfected euploid hippocampal cells maintained in B27-supplemented medium (Eu+B27) were used as a control. Results of TUNEL at 72 hours post-transfection (five days in vitro) are expressed as percentage of apoptotic (TUNEL-positive) cells+SEM (=$p<0,01$ vs. control Ts16 non-transfected; +=$p<0.01$ vs. pJHL-15-transfected cells, by ANOVA with Tukey-Kramer post-test).

The trisomy 16 (Ts16) mouse is considered to be a model of Down's syndrome (DS; trisomy 21) (Coyle et al., 1988, Trends Neurosci., 11:390-394) with a cluster of genes and loci on chromosome 16 that are also located on the long arm of human chromosome 21 (Sawa et al., 1999, J. Neural Transm [Suppl], 57:87-87). DS individuals develop Alzheimer's disease (AD) by their fifth decade (Sawa et al., 1999, J. Neural Transm [Suppl], 57:87-87), suggesting that this genetic defect also confer increased vulnerability to neurodegeneration. Cultured hippocampal neurons from Ts16 mouse exhibit augmented cell death when compared to eupoid cells even in the presence of adequate trophic support (Bambrick et al., 1999, J. Neurochem., 72:1769-1772). Accordingly, in this series of experiments designed to examine whether ICP10PK can block apoptosis in neuronal cells, we used primary hippocampal cultures from Ts16 mice, established as described (Bambrick et al., 1999, J. Neurochem., 72:1769-1772). The cells were transfected with pJW17 or pJHL15 at two days in culture and maintained in B27-supplemented medium for the duration of the experiment. Non-transfected (Ts16) neurons evidenced an accelerated death rate (76.2±2.3%, 53.7±2.8%, and 41.4±2.3% survival it 24, 48 and 72 hours, respectively) relative to eupoid neurons (Eu-±B27) (93.8±1.7% 88.7±3.1%, and 80.6±2.7% survival at 24, 48, and 72 hours, respectively) (p<0.01 by ANOVA) (FIGS. 13 and 14A). Similar cell deaths kinetics were seen for pJHL15-transfected Ts16 neurons (73.8±3.0%, 54.9±3.2% and 43.8±3.7%, at 24, 48 and 72 hours, respectively) (p>0.05 vs. non-transfected Ts16 neurons by ANOVA) (FIGS. 13 and 14B). By contrast, the survival of pJW17-transfected Ts16 neurons (93.5±1.5%, 83.9±2%, and 75.6±2.2% at 24, 48 and 72 hours (p>0.05 vs. non-transfected Ts16 neurons (93.5±1.5%, 83.9±2%, and 75.6±2.2% at 24, 48 and 72 hours, respectively) was similar to that of Eu+B27 cells and significantly (p<0.001., by ANOVA) increased than that of non-transfected Ts16 neurons (FIGS. 13 and 14C). The mechanism of Ts16 cell death was examined by TdT-medicated dUTP nick end labeling (TUNEL), an assay that is widely considered to be specific for apoptosis (Gavrieli et al., 1992, J. Cell. Biol., 119:493-501). Ts16 cultures (non-transfected or transfected with pJW17 or pJHL15 expression vectors) were fixed with 4% paraformaldehyde at day five in vitro (72 hours post-transfection) and TUNEL was carried out using the In Situ Cell Death Detection Kit-AP (Roche Molecular Biochemicals) according to the manufacturer instructions. Apoptotic cells (characterized by a dark nuclear precipitate) and non-apoptotic cells (unstained or displaying a diffuse, light and uneven cytoplasmic staining) were counted in five randomly chosen microscopic fields (containing at least 250 cells). Results are expressed as percentage of apoptotic cells±SEM. The proportion of TUNEL-positive cells (apoptotic) in non-transfected (43±3.4%) and pJHL15-transfected (39±1%) correlate well (within the limits of experimental error) with the percentage of dead cells obtained by counting the morphologically viable cells (approximately 60% death at day 5 in vitro or 72 hours post-transfection). The difference in absolute values may be due to the loss of some cells during the fixation procedure and/or the apoptotic process itself. By contrast, the percentage of apoptotic cells was significantly lower (p<0.001, by ANOVA) in pJW17-transfected Ts16 cells (9.4±1.1%) similar to that obtained for euploid cultures maintained in MEM with B27 supplement (Eu+B27) (9.6±2%) (FIG. 15). These data indicate that ICP10PK blocks the apoptotic death of Ts16 neurons. Similar results were obtained in three independent experiments.

Figure 16:
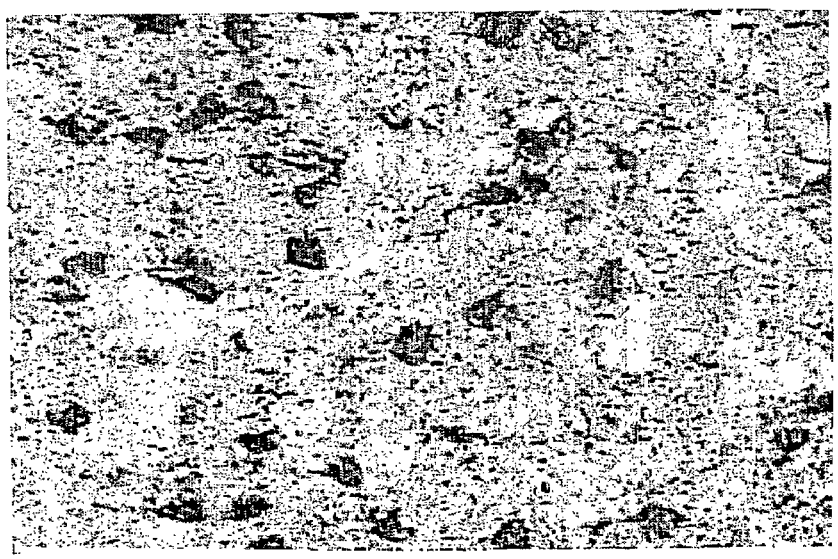
FIG. 16 an image of a photomicrograph depicting staining of ICP10PK in mouse hippocampal neurons. Mice (C57/B1) were infected intranasally with ICP10deltaRR or phosphate buffer saline (PBS; control). At seven days post-infection, mice were anesthetized with ether and perfused with 4% paraformaldehyde. Coronal brain sections (20 micrometer) were immunostained with antibody specific for ICP10 by the immunoperoxidase method. Staining was observed in the hippocampi of mice infected with ICP10deltaRR virus, but not in mock (PBS)-infected mice.

To examine whether the anti-apoptotic protein ICP10PK can be delivered to the CNS Using the ICP10deltaRR vector, the natural route of transmission of HSV to the CNS by means of olfactory nerves and tracts was mimicked. Mice were infected intranasally with various amounts of ICP10deltaRR virus or phosphate buffer saline (as a control) and sacrificed one week later. Coronal sections of the brains were immunostained with antibody specific for ICP10 (FIG. 16). ICP10deltaRR virus is growth compromised in vitro and in vivo following inoculation. Significantly, the intranasally infected mice were free of neurological impairments or other untoward effects associated with HSV-2 infection. Data suggest that peripheral (intranasal) administration of ICP10ΔPK with the ICP10deltaRR vector induces protein expression at least up to one week in hippocampus and related limbic structures.

Example 3

A bcl-2-Expressing HSV-2 ICP10deltaRR Mutant Virus

To construct the ICP10deltaRR mutant virus, the LacZ coding gene in the ICP10deltaRR plasmid is replaced with the gene encoding bcl-2, and the virus is rescued by recombination screening for white plaques. The strategy is similar to that which was used to construct the ICP10deltaPK virus (Smith et al., 1998, J. Virol., 72:9131-9141; Peng et al., 1996, Virology, 216:184-196).

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

We claim:

1. A method of inhibiting neuronal apoptosis in a mammal, comprising administering to said mammal an apoptosis-inhibiting amount of a polypeptide consisting of amino acids 1 to 411 of SEQ ID NO: 2 wherein said polypeptide is administered directly into cells.

2. A method of inhibiting neuronal apoptosis in a mammal, comprising administering to said mammal an apoptosis-inhibiting amount of a polypeptide consisting of amino acids 1 to 411 of SEQ ID NO: 2 fused to a bcl-2 polypeptide, or a mutant, variant, homolog, or fragment thereof having anti-apoptotic activity wherein said polypeptide is administered directly into cells.

3. The method of claim 1, wherein said neuronal apoptosis is associated with a neurodegenerative disorder.

4. The method of claim 3, wherein said neurodegeneranve disorder is Alzheimer's disease (AD), lateral sclerosis (ALS), Down syndrome (DS), diabetic neuropathy, Parkinson's disease (PD) or Huntington disease (HD).

5. The method of claim 1, wherein said neuronal apoptosis is associated with an injury of the central or peripheral nervous system.

6. The method of claim 5, wherein said injury is a result of stroke, cerebral ischemia, or chemical and/or physical trauma.

7. The method of claim 1, additionally comprising administering a polypeptide encoded by a nucleic acid encoding bcl-2 or any mutant, variant, homolog, or fragment thereof having anti-apoptotic activity.

8. A method of inhibiting apoptosis in a mammal comprising administering to said mammal an apoptosis-inhibiting amount of a polypeptide which consists of amino acids 1 to 411 of SEQ ID NO: 2 wherein said polypeptide is administered directly into cells.

9. A method of inhibiting apoptosis in a mammal, comprising administering to said mammal an apoptosis-inhibiting amount of a polypeptide consisting of amino acids 1 to 411 of SEQ ID NO: 2 fused to a bcl-2 polypeptide, or any mutant, variant, homolog, or fragment thereof having anti-apoptotic activity wherein said polypeptide is administered directly into cells.

* * * * *

UNITED STATES PATENT AND TRADEMARK OFFICE
CERTIFICATE OF CORRECTION

PATENT NO. : 7,482,318 B2  Page 1 of 1
APPLICATION NO. : 10/333607
DATED : January 27, 2009
INVENTOR(S) : Aurelian et al.

It is certified that error appears in the above-identified patent and that said Letters Patent is hereby corrected as shown below:

Col. 43, line 46 reads "The method of claim 3, wherein said neurodegeneranve", should read --The method of claim 3, wherein said neurodegenerative--.

Signed and Sealed this

Twenty-second Day of September, 2009

David J. Kappos
*Director of the United States Patent and Trademark Office*